United States Patent [19]
Nesburn et al.

[11] Patent Number: 5,660,692
[45] Date of Patent: *Aug. 26, 1997

[54] METHOD OF CROSSLINKING AMINO ACID-CONTAINING POLYMERS USING PHOTOACTIVATABLE CHEMICAL CROSSLINKERS

[75] Inventors: Anthony B. Nesburn, Malibu, Calif.; Michael B. Gorin, Pittsburgh, Pa.; M. Cristina Kenney, Malibu; Ezra Maguen, Los Angeles, both of Calif.

[73] Assignee: Cedars-Sinai Medical Center, Los Angeles, Calif.

[*] Notice: The term of this patent shall not extend beyond the expiration date of Pat. No. 5,024,742.

[21] Appl. No.: 482,104

[22] Filed: Jun. 7, 1995

Related U.S. Application Data

[63] Continuation-in-part of Ser. No. 170,602, Dec. 21, 1993, Pat. No. 5,431,790, which is a continuation of Ser. No. 659,497, Feb. 22, 1991, Pat. No. 5,294,314, which is a continuation of Ser. No. 159,603, Feb. 24, 1988, Pat. No. 5,024,742.

[51] Int. Cl.$^6$ ............................... C08K 5/00
[52] U.S. Cl. ............. 204/157.68; 530/356; 530/409
[58] Field of Search ............... 204/157.68; 530/356, 530/409

[56] References Cited

U.S. PATENT DOCUMENTS

| | | | |
|---|---|---|---|
| 4,505,855 | 3/1985 | Bruns et al. | 204/159.14 |
| 4,511,478 | 4/1985 | Nowinski et al. | 210/691 |
| 4,597,999 | 7/1986 | Lingwood | 204/157.68 |
| 4,621,631 | 11/1986 | Paques | 128/156 |
| 4,883,487 | 11/1989 | Yoshizato | 623/15 |
| 5,024,742 | 6/1991 | Nesburn et al. | 204/157.68 |
| 5,294,314 | 3/1994 | Nesburn et al. | 204/157.68 |
| 5,431,790 | 7/1995 | Nesburn et al. | 204/157.68 |

FOREIGN PATENT DOCUMENTS

| | | |
|---|---|---|
| 0246013 | 11/1987 | European Pat. Off. |
| 1015284 | 12/1965 | United Kingdom. |

OTHER PUBLICATIONS

Bloomfield et al., Amer. J. Ophthal. 55:742–748 (1963) *no month available.
Bonchek et al., Ann. Surg. 165:420–424 (1967) *no month available.
Branch et al., Surgery 19:460–466 (1946) *no month available.
Dupuis et al., Can. J. Biochem. Cell Biol. 61(2–3):99–106 (1983) *no month available.
Elsdale et al., Cell Biol. 54:626–637 (1972) *no month available.
Forabosco et al., Bull. Group Int. Rech. sc. Stomat.et Odont 27:171–180 (1984) *no month available.
Geggel et al., Investigative Ophthalmology and Visual Sciences 26(6):901–905 (1985) *no month available.
Ikossi-O'Connor et al., Journal of Surgical Oncology 23:151–152 (1983) *no month available.
Ji, T.H., Biochimica et Biophysica Acta 559:39–69 (1979) *no month available.
Matsumoto, T., Med. Exam Pub. Co. N.Y. (1972) *no month available.
Miyata et al., Biochimica et Biophysica Acta 229:672–680 (1971) *no month available.

(List continued on next page.)

*Primary Examiner*—Kathryn L. Gorgos
*Assistant Examiner*—Kishor Mayekar
*Attorney, Agent, or Firm*—Lyon & Lyon LLP

[57] ABSTRACT

A method for molecularly crosslinking amino acid-containing polymers by photoactivating chemical crosslinkers which have been combined with the polymers. Collagen crosslinked by this method can be used as a bioadhesive for sutureless closures of the skin and eye or as a superhydrated material for contact lenses, moist bandage contact lens, lens or corneal implant material, or as a drug delivery mechanism.

26 Claims, 14 Drawing Sheets

OTHER PUBLICATIONS

Nimni, M. Biorheology 17:51–82 (1980) *no month available.

Parry et al., Brit J. Ophthal 30:176–178 (1946) *no month available.

Partis et al., Journal of Protein Chemistry 2(3):263–277 (1983) *no month available.

Peters et al., Ann. Rev. Biochem. 46:523–51 (1977) *no month available.

Selverstone et al., Arch. Surg. 84:98–102 (1962) *no month available.

Town, Trans. Amer. Acad. Ophthal. Otolaryng. 54:131–133 (1949) *no month available.

Wold, J. Biol. Chem. 236(1):106–111 (1961) *no month available.

Young et al., War. Med. 6:80–85 (1944) *no month available.

UNCROSSLINKED COLLAGEN

CROSSLINKED COLLAGEN

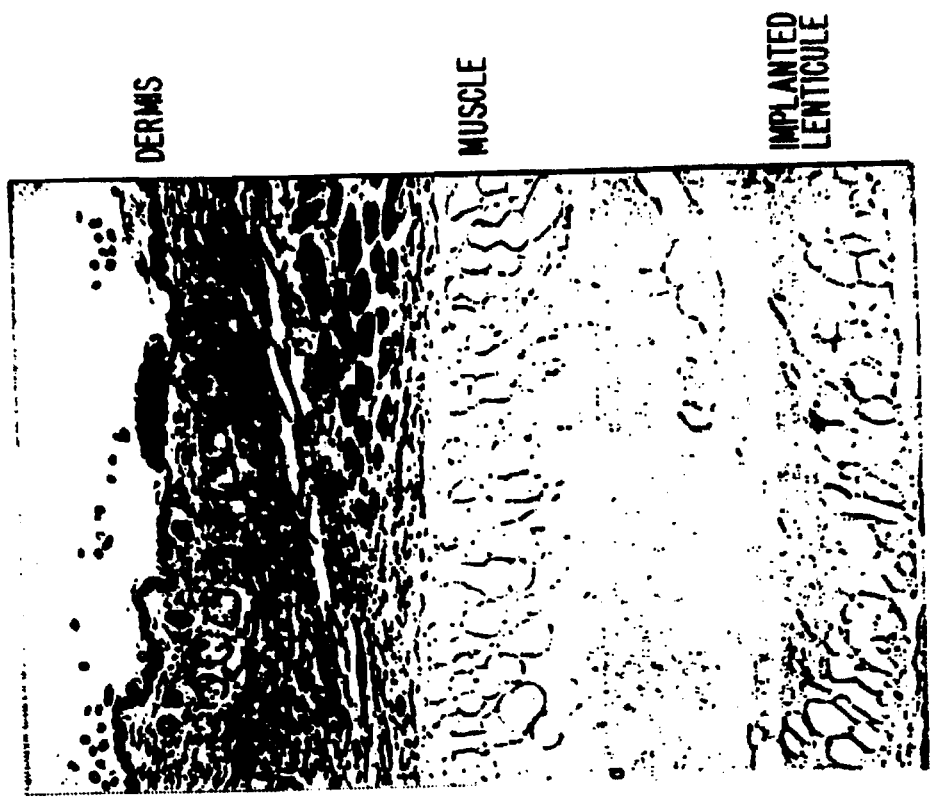
FIG. 2b. UNCROSSLINKED COLLAGEN
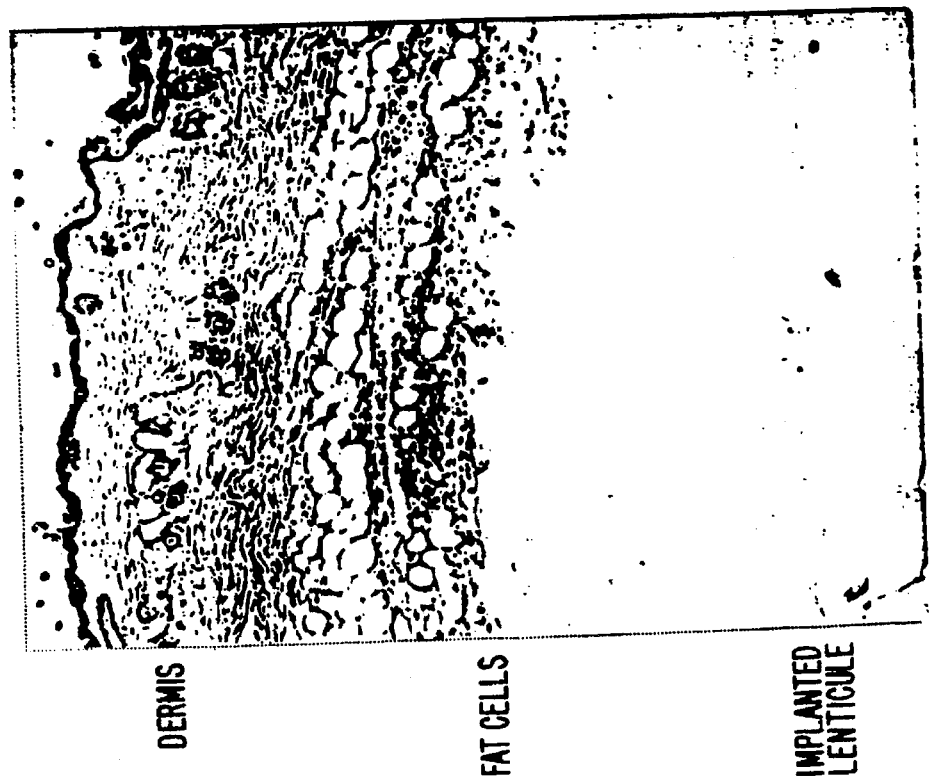
FIG. 2a. CROSSLINKED COLLAGEN

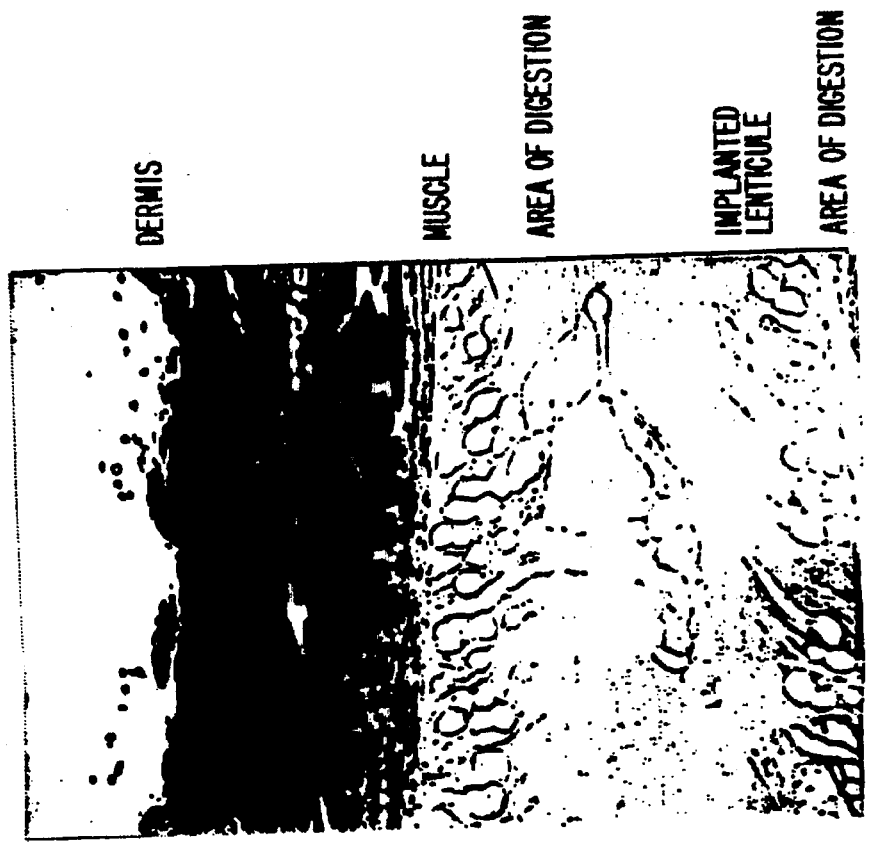
FIG. 3b. UNCROSSLINKED COLLAGEN
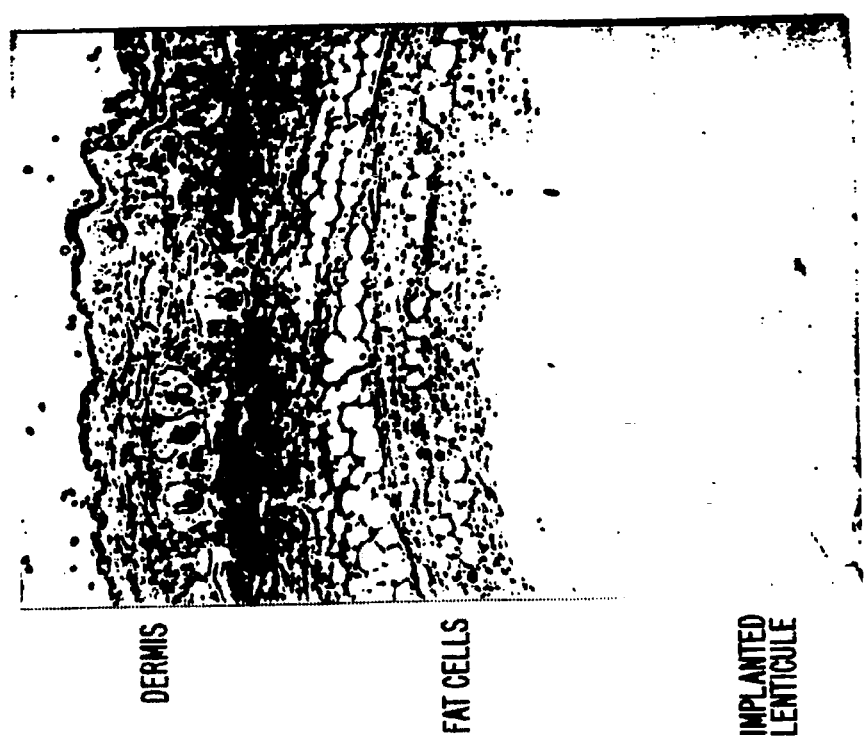
FIG. 3a. CROSSLINKED COLLAGEN

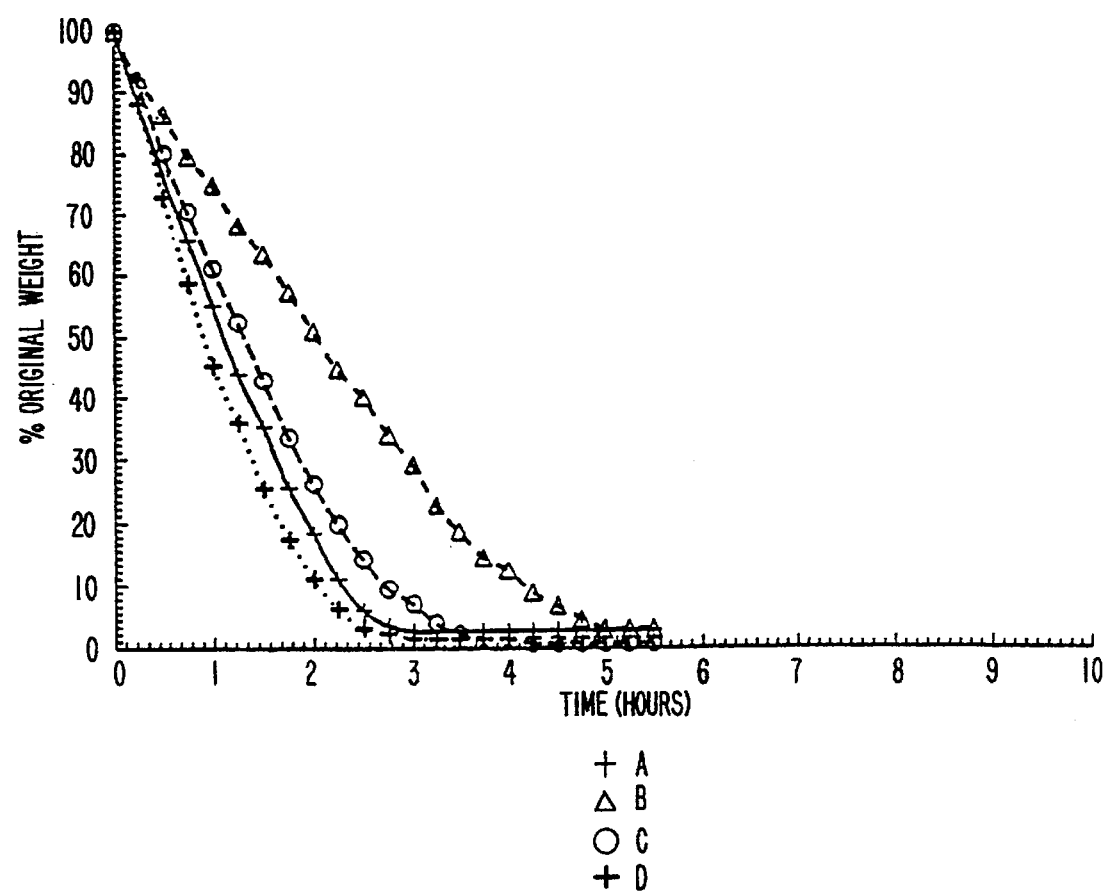

LOW POWER MAGNIFICATION

HIGHER POWER MAGNIFICATION

FIG. 7.

| IMPLANTED MATERIAL | PERIOD AFTER IMPLANTATION | ANTIBODIES TITER |
|---|---|---|
| STRAIGHT COLLAGEN | TWO WEEKS | — |
|  | ONE MONTH | — |
|  | TWO MONTHS | 1/64 – 1/128(±) |
|  | THREE MONTHS | MOUSE IS DISAPP. |
| CROSSLINKED COLLAGEN | TWO WEEKS | — |
|  | ONE MONTH | — |
|  | TWO MONTHS | 1/64 – 1/128(±) |
|  | THREE MONTHS | 1/128 – 1/256(±) |
| FILTRATED FISH GELATIN | TWO WEEKS | — |
|  | ONE MONTH | — |
|  | TWO MONTHS | 1/128 |
|  | THREE MONTHS | 1/128 – 1/256(±) |
| UNFILTRATED FISH GELATIN | TWO WEEKS | — |
|  | ONE MONTH | — |
|  | TWO MONTHS | 1/128 |
|  | THREE MONTHS | 1/256 – 1/512(±) |
| COVER: FF+CF+GAGs IMPLANTS: FC | TWO WEEKS | — |
|  | ONE MONTH | — |
| FF | TWO WEEKS | — |
|  | ONE MONTH | — |
| CC | TWO WEEKS | 1/32 |
|  | ONE MONTH | 1/32 – 1/64 |
| INJECTION (UNCROC.) FF+FC | ONE MONTH | CF- (±); FF (-) |
|  | TWO MONTHS | CF- 1/128; FF (-) |
| FF+CF+GAGs | ONE MONTH | CF- 1/128; FF (-) |
|  | TWO MONTHS | CF- 1/256; FF (-) |
| INJECTION: FF + 0.25% GLUTARALDEHYDE | ONE MONTH | — |
|  | TWO MONTHS | — |

Legend
- SC   Straight collagen
- CC   Crosslinked collagen (I + V)
- SF   Straight fish gelatin
- FF   Filtrated fish gelatin (>100.000d)
- FC   Filtrated calf gelatin (>300.000d)
- FF + FC   Filtrated fish gelatin (>300.000d) + filtrated calf gelatin (>300.000d) (3:1)
- Ch.S.   Chondroitin sulfate
- HA   Hyaluronic Acid
- FB   Foreign body
- COVER   C.F. 82.48% + Ch.S. 8.23% + H.A. 9.28%

FIG. 8a.

■ IRRITATING SUBSTANCES
■ TOXIC SUBSTANCES

| TRADE NAME | STRUCTURAL FORMULA AND CHEMICAL NAME | MW | SPACE ARM | ADDITIONAL INFORMATION |
|---|---|---|---|---|
| HSAB | N-HYDROXYSUCCINIMIDYL-4-AZIDOBENZOATE | 250.21 | 8.0 | PHOTOREACTIVE ■ |
| SULFO-HASAB | N-HYDROXYSULFOSUCCINIMIDYL-4-AZIDOBENZOATE | 362.25 | 9.0 | PHOTOREACTIVE WATER-SOLUBLE ■ |
| SIAB | N-SUCCINIMIDYL(4-IODOACETYL)AMINOBENZOATE | 402.15 | 10.5 | ■ |

FIG. 8b.

| TRADE NAME | STRUCTURAL FORMULA AND CHEMICAL NAME | MW | SPACE ARM | ADDITIONAL INFORMATION |
|---|---|---|---|---|
| SAND | SULFSOUCCINIMIDYL 2-(m-AZIDO-O-NITROBENZAMIDO)-ETHYL-1.3'-DITHIOPROPIONATE | 570.52 | 18.5 | PHOTOREACTIVE ALLOWS 320-350nm FOR PHOTOLYSIS CLEAVABLE BY THIOLS |
| SULFO-SANPAH | SULFSOUCCINIMIDYL 6-(4'-AZIDO-2'-NITROPHENYLAMINOL)HEXANOATE | 492.39 | 18.2 | PHOTOREACTIVE WATER-SOLUBLE |
| DFDNB | 1,5-DIFLUORO-2,4-DINITROBENZENE | 492.39 | 18.2 | HOMOBIFUNCTIONAL |

FIG. 9.

| | M.W./res. | Type I a1 res./1000 | M.W. | Type I a2 res./1000 | M.W. | Type V a1 res./1000 | M.W. | Type V a2 res./1000 | M.W. |
|---|---|---|---|---|---|---|---|---|---|
| Hyp | 204 | 86 | 17544 | 85 | 17340 | 108 | 22032 | 107 | 21828 |
| Asp | 133 | 45 | 5985 | 47 | 6251 | 51 | 6783 | 55 | 7315 |
| Thr | 119 | 16 | 1904 | 17 | 2023 | 22 | 2618 | 27 | 3213 |
| Ser | 105 | 34 | 3570 | 24 | 2520 | 26 | 2730 | 34 | 3570 |
| Glu | 147 | 77 | 11319 | 71 | 10437 | 99 | 14553 | 90 | 13230 |
| Pro | 189 | 135 | 25515 | 120 | 22680 | 119 | 22491 | 92 | 17388 |
| Gly | 75 | 327 | 24525 | 328 | 24600 | 220 | 16500 | 318 | 23850 |
| Ala | 89 | 120 | 10680 | 101 | 8989 | 46 | 4094 | 59 | 5251 |
| Val | 116 | 18 | 2088 | 34 | 3944 | 19 | 2204 | 30 | 3480 |
| Ile | 130 | 9 | 1170 | 17 | 2210 | 20 | 2600 | 18 | 2340 |
| Leu | 130 | 21 | 2730 | 34 | 4420 | 40 | 5200 | 37 | 4810 |
| Tyr | 187 | 4 | 748 | 3 | 561 | 1 | 187 | - | - |
| Phe | 231 | 12 | 2772 | 16 | 3696 | 12 | 2772 | 12 | 2772 |
| Hyl | 162 | 5 | 810 | 11 | 1782 | 36 | 5832 | 25 | 4050 |
| Lys | 146 | 32 | 4672 | 21 | 3066 | 7 | 1022 | 18 | 2628 |
| His | 158 | 3 | 474 | 8 | 1264 | 19 | 3002 | 10 | 1580 |
| Arg | 159 | 50 | 7959 | 57 | 9063 | 48 | 7632 | 57 | 9063 |
| Met | 149 | 7 | 1022 | 4 | 596 | 7 | 1022 | 10 | 1490 |
| Σ | | | 125499 | | 125442 | | 123295 | | 127858 |

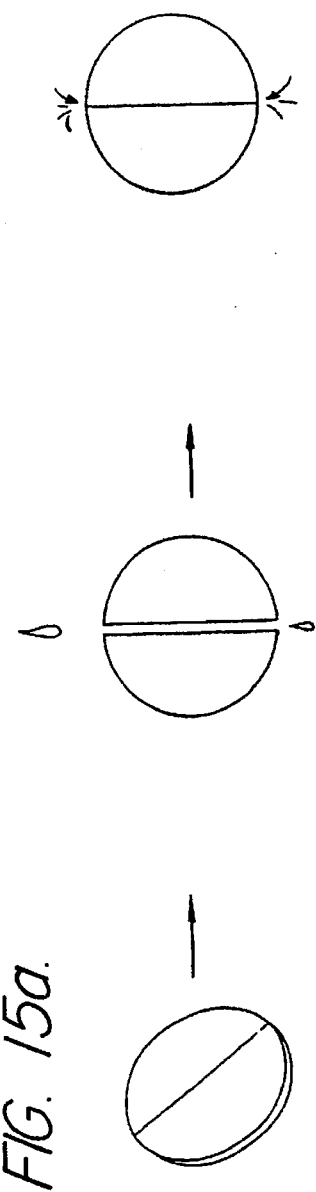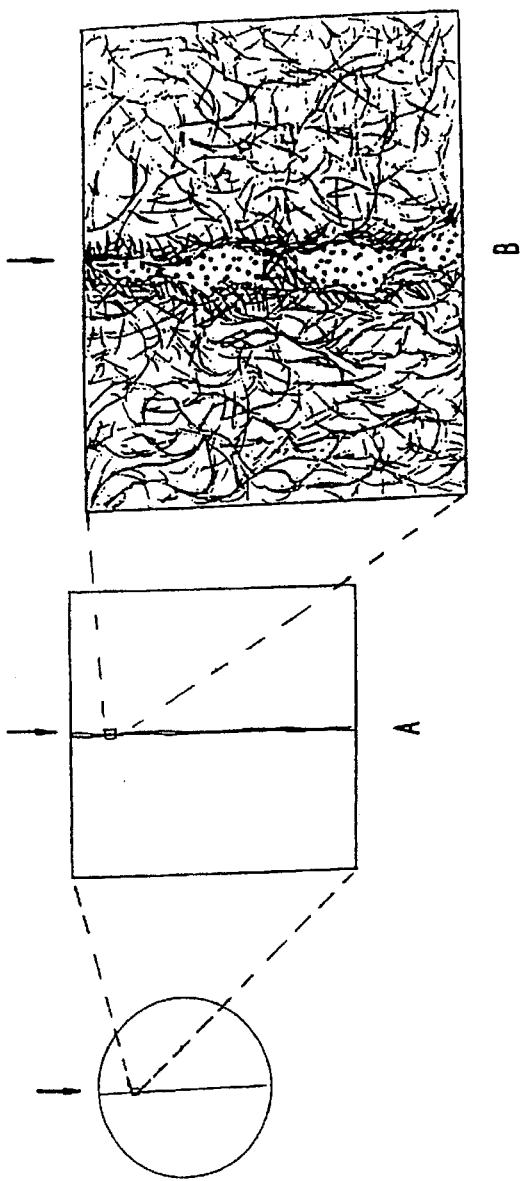
FIG. 15a.
FIG. 15b.

METHOD OF CROSSLINKING AMINO ACID-CONTAINING POLYMERS USING PHOTOACTIVATABLE CHEMICAL CROSSLINKERS

This application is a continuation-in-part of U.S. application Ser. No. 08/170,602, filed Dec. 21, 1993, now U.S. Pat. No. 5,431,790, which is a continuation of U.S. application Ser. No. 07/659,497, filed Feb. 22, 1991, now U.S. Pat. No. 5,294,314, which is a continuation of U.S. application Ser. No. 159,603, filed Feb. 24, 1988, now U.S. Pat. No. 5,024,742, all of which parent applications are expressly incorporated herein by reference.

FIELD OF THE INVENTION

This invention relates to methods for molecularly crosslinking amino acid-containing polymers by photoactivating chemical crosslinking reagents which have been combined with the polymers. More particularly, the invention relates to methods for molecularly crosslinking collagen by photoactivating heterobifunctional crosslinking reagents which have been combined with collagen. Upon photoactivation, reactive groups on these bifunctional reagents crosslink the collagen by forming bridges between amino acid side chains on the collagen molecule.

BACKGROUND OF THE INVENTION

Chemical crosslinkers have been used to study the molecular organization of cell membranes and to understand the way in which various molecules interact with one another at the inner or outer surface of the membrane (Peters, K., Richards, F. M., Ann. Rev. Biochem. 46:523–51 (1977), incorporated herein by reference). Protein structural studies utilizing chemical crosslinking began during the 1950s with the work of Zahn (Angew. Chem. 67:561–572, 1955; Makromol. Chem. 18:201–216, 1955; Makromol. Chem. 72:126–152 (1958), incorporated herein by reference) and continued in the 1960s, primarily with the work of Wold and his colleagues (J. Biol. Chem. 236:106–111 (1961), incorporated herein by reference). In addition, crosslinkers have been used to artificially crosslink and stabilize tissue (Nimni, M., Biorheology, 17:51–82 (1980)). Crosslinking techniques for the membrane system studies discussed above have made use of bifunctional reagents, which are classified as either homo- or heterobifunctional. Homobifunctional reagents have two identical reactive sites. Heterobifunctional reagents carry two dissimilar binding sites, one photosensitive and one conventional site. In general, both types of bifunctional reagents act to form chemical crosslinks by introducing bridges between amino acid chains.

The utility of the homobifunctional reagents as crosslinkers in membrane studies has been limited due to several potential inherent problems including random collisional crosslinks, long reaction time, difficulty in controlling reactions and nonselective crosslinking. Random collision dependent crosslinks can occur at a significant frequency, since molecules nonspecifically crosslink during random collisions in fluid membranes. Such indiscriminate formation of crosslinks can result in a high multiplicity of crosslinked products which are difficult to analyze. It is possible, therefore, that low yield crosslinked products would go undetected. These random collisional crosslinks were avoided in some membrane systems with the use of rapidly crosslinking photosensitive agents. (Ji, T. H., Biochimica et Biophysical Acta, 559:39–69 (1979), incorporated herein by reference).

In contrast, crosslinking with photosensitive heterobifunctional reagents, can be easily, rapidly and sequentially controlled. Crosslinking with heterobifunctional reagents is accomplished by binding the conventional site on the reagent to one amino group via an amide bound, leaving the second photoactivatable site unbound. Upon photoactivation by the use of ultraviolet or visible irradiation, the photoactivatable site is converted to a species of very high chemical reactivity, which then forms a covalent linkage with another amino group. The absorption of ultraviolet or visible radiation by the bifunctional reagent can give rise to two general classes of species produced by cleavage of chemical bonds. Fragmentation can be either at a single bond, resulting in the formation of two free radicals, or at a double bond to carbon or nitrogen. Two types of photosensitive groups are known that result from cleavage at a double bound to carbon or nitrogen: an azide derivative and a diazo derivative. Nitrenes are generated from azides, and carbenes are generated upon photolysis of diazo derivatives. Both nitrenes and carbenes are compounds of very high chemical reactivity.

A common method used for photoactivation of heterobifunctional compounds is irradiation with a short wave ultraviolet lamp, for example, mineral light USV-11. The half time of photolysis with this lamp varies depending on the reagents and is in the order of 10 to 50 seconds. An alternative method, which has several advantages, is flash photolysis for an extremely short period, normally on the order of milliseconds.

Collagen is the single most abundant animal protein. It is the main structural component of mammalian tissues and accounts for about 30% of all mammalian proteins (Nimni, M., Biorheology, 17:51–82 (1980), incorporated herein by reference). The molecular structure of collagen consists of three intertwining helical polypeptide chains about 1,050 residues long, wound around each other to form a triple helix.

There is a great amount of uniformity in the amino acid composition of collagen. Glycine forms about 33 percent and proline and hydroxyproline form about 25 percent of the total amount of residues in the polypeptide chains. Proline and hydroxyproline contribute to the rigidity of the molecule in that the beta C is linked to the peptide nitrogen by the side chain, forming a five membered ring thus allowing relatively little freedom of rotation. It is this locking effect by proline and hydroxyproline residues, and the hydrogen bond formation by the hydroxyl group of hydroxyproline, which gives collagen its great stability. The other amino acid residues in the structure include 10 percent alanine and 20 percent polar side chains of arginine, lysine, asparagine and glycine. These do not play a particularly important role in the triple helix but nevertheless are important in the intermolecular linkages which lead to fiber formation.

Crosslinking of the collagen molecules occurs extracellularly and leads to formation of the collagen fiber. This characteristic fiber organization is responsible for the functional integrity of tissues such as bone, cartilage, skin and tendon, and for the structural integrity of blood vessels and most organs.

Both intra- and intermolecular crosslinks in collagens are derived from lysine and hydroxylysine residues. Intramolecular crosslinks are formed when specific lysine and hydroxylysine residues in collagen are oxidatively deaminated to peptide bound aldehydes. Copper, a cofactor with the enzyme lysyl oxidase, causes this modification to take place. The actual formation of the crosslinks takes place via aldol condensation, a spontaneous non-enzymatic reaction where the lysines which are located near the end-terminal region are converted to aldehydes. Intermolecular crosslinks are formed between peptide bound aldehydes and unmodified amino groups of other lysine and hydroxylysine residues. These are the Schiff base type crosslinks, otherwise known as aldamine crosslinks (aldehyde and amino group). This type of crosslink is also considered to be the most physiologically important.

Crosslinking of collagen is a prerequisite for the collagen fibers to withstand the physical stresses to which they are exposed. In past investigations, chemical agents, in particular glutaraldehyde, were found to have application for biosynthesis of intramolecular and intermolecular crosslinks. Artificial crosslinking of collagen with glutaraldehyde has been used commercially to stabilize pig heart valves which are then used in artificial valve replacements (Nimni, M., Biorheology, 17:51–82 (1980), incorporated herein by reference). The collagen is crosslinked in this technique with 25 percent glutaraldehyde (commercial) at a neutral pH. The exact glutaraldehyde chemistry of the crosslinking is not clear but Schiff base linkages of glutaraldehyde with two lysine residues are formed.

Many studies have been conducted to develop a substance, either natural or synthetic, which can be employed as a non-traumatic means to help repair tissues after surgery. Major interest in the surgical use of polymeric adhesive materials began in the early sixties (Silverstone. et al., Arch. Surg. 81:98 (1962), incorporated herein by reference). Initial work was confined to water-soluble systems such as casein and polyvinyl alcohol, but later was expanded to include all available synthetic adhesives and other plastics. Effort at this point was limited to materials with no known local or general toxicity. The 1962 effort of Silverstone and his coworkers was directed more towards wider application of bonding techniques in arterial surgery. In addition to the reinforcement of aneurysms unsuitable for resection, the uses contemplated included reinforcement of junctions after arterial suture or graph, and non-suture anastomosis of small arteries. Although other materials have been investigated, the most widely used of the tissue adhesives are the cyanoacrylates. These are a homologous series of organic molecules which polymerize and adhere to moist living tissues. Methyl-alphacyanoacrylate (MCA) in particular, has been used since 1960 by many investigators as a tissue adhesive for non-suture of bones. MCA is a fluid, monomeric material which under mild pressure, polymerizes in a matter of seconds to produce a thin, strong, adherent film. Although MCA has been shown to be histotoxic, work with higher homologues of the n-alkyl-alphacyanoacrylates has indicated that if one proceeds up the homologous series, this histotoxicity decreases. The toxic effects of synthetic polymers on tissues are related in part to their breakdown products and to the rate at which they are released. All of the polycyanoacrylates degrade in an aqueous medium by the same mechanism—the cleavage of the carbon-to-carbon backbone of the polymer, and the ultimate releasing of formaldehyde and other breakdown products. This mechanism of degradation is essentially the same for all the alkyl cyanoacrylates, though the rate is quite different and depends on the nature of the radical.

It has been reported that the less toxic higher homologues of the cyanoacrylates instantaneously polymerize on tissue substrates and thereby are more effective in inducing homeostasis. Instantaneous polymerization, however, is a disadvantage in surgical applications where it is required to bond two surface's together, or in adhering cut surfaces of an organ. In these instances, one requires sufficient working time to approximate the surfaces of the tissues before adhesion is permitted to take place.

In order to accommodate these surgical requirements, application techniques of tissue adhesives have been investigated (Matsumoto, T., Tissue Adhesives Insurgent, Med Exam. Pub. Co., New York (1972), incorporated herein by reference). Tissue adhesives were applied using a spray gun or by a drop method. Polymerization of the adhesive occurred more rapidly when it was applied by spraying. The difference in rates of polymerization was explained by the fact that on spraying, the monomers formed a spreading film, making more surface available to the initiator and thereby a more rapid polymerization rate.

In many surgical techniques the use of the spray method discussed above has a distinct advantage because it is not possible to apply the monomer uniformly and in a thin film with the drop method. Spraying, however, has one disadvantage, in that the monomer polymerizes more rapidly and makes it necessary for the surgeon to work faster. The advantages of and need for an adhesive wherein the surgeon can control the polymerization rate is therefore clear.

In addition, although the reports indicate that cyanoacrylate tissue adhesives offer advantages when used for repair or homeostasis of injured organs, it is known that the presence of the polymer fragment between the incised skin delays wound healing. This is because the polymer fragments prevent the proliferation of fibroblast and microcirculatory vessels bridging the wounded surfaces. Studies conducted comparing the tensile strength of wounds closed by sutures versus cyanoacrylate adhesives, have shown that the glue remains in the tissue for long periods of time, and maximal wound strength is obtained later than for suture closure.

Application of cyanoacrylate adhesives in ophthalmological procedures was introduced in 1963 (Bloomfield, S. et al., Amer. J. Ophthal., 55:742–748 (1963), incorporated herein by reference). Since the maintenance of a delicate metabolic and pressure balance within the eye is vital to its optical and electrophysiological function and depends on the integrity of the outer coat, considerable attention in ophthalmology has always been directed towards methods of repair of any process which disrupts the cornea or sclera. Early experience with cyanoacrylate adhesives in the eye was not particularly encouraging. Methyl-2-cyanoacrylates were found to have suitable bond strength, but they proved too toxic.

Over the past century, a number of substances other than the cyanoacrylates have been proposed for sticking one tissue to another, but as with the cyanoacrylates, none appear to have been entirely successful.

Crosslinked gelatins are a leading contender with the cyanoacrylates for the attention and interest of investigators working on tissue bioadhesives. Gelatin is a naturally occurring animal protein with innate adhesive properties. Molecular weights of gelatins range between 30,000 and 120,000 and chemically it is somewhat similar to connective tissue. In 1965, Braunwald and Tatooles (Surgery, 19:460 (1946), incorporated herein by reference) reported the successful use of crosslinked gelatin to control hemorrhage from wounds of the liver and the kidney in dogs. Still later, Bonchek and Braunwald (Ann. Surg., 165:420 (1967), incorporated herein by reference) also describe the use of crosslinked gelatin to repair incisions in dogs. The main problem with gelatin as a bioadhesive however, is that it is highly susceptible to enzymatic degradation.

Other substances with some adhesive properties have been used to help ocular wounds heal quickly and firmly.

Parry and Laszlo reported the use of thrombin for a quick and efficient sealing of conjunctival wounds in corneal scleral incisions in cataract surgery (Brit. J. Opthal., 30:176–178 (1946), incorporated herein by reference). Town used fibrin in cataract, glaucoma and traumatic plastic surgery and in keratoplasty (Trans. Amer. Acad. Ophthal. Otolaryng., 54:131–133, (1949), incorporated herein by reference). But Young and Favata pointed out that thrombin imparts less tensile strength than ordinary suture materials (War. Med., 6:80–85 (1944), incorporated herein by reference). Another adhesive that has been investigated is fibrinseal (FS) which is a natural adhesive material composed of fibrinogen, factor VIII, platelet growth factor, anti-plasmin thrombin, and calcium chloride. FS has been utilized in vascular surgery to limit blood loss and minimize the amount of vessel trauma and foreign-body reaction by decreasing the number of sutures necessary to achieve a technically satisfactory arterial anastomosis. However, FS causes an increase in the amount of lymphocytic infiltrate in specimens early in the post operative period. As the authors admit, detailed studies to define its role and drawbacks are in order (Ikeossi-O'Connor, M. G., Journal of Surgical Oncology, 23:151–152 (1983), incorporated herein by reference).

A human fibrin glue has been used in oral surgery (Bull. Group. int. Rech. sc. Stomat. et Odont., 27:171–180 (1984), incorporated herein by reference). The substance is made up of two components. One, is highly concentrated fibrinogen and factor VIII together with other plasma proteins, such as albumin and globulin. The second component is a solution of thrombin and calcium chloride, a catalytic agent. The Factor VIII induces the collagen present in the connective tissue to polymerize with the fibrin, forming a bridge between collagen and fibrin. Some known disadvantages of this fibrin glue are that once prepared, it must be used within a short time (so the surgeon must possess accuracy and speed in the operating technique), and the possible transmission of the hepatitis and AIDS viruses.

The foregoing discussion describes the efforts to use a variety of substances of both natural and artificial origin as tissue adhesives. None of these efforts have been completely successful. There still remains both a need for, and a desire for, a tissue adhesive which is simple and practical in application, which is not toxic, which does not retard wound healing, which is readily and harmlessly absorbed and eliminated to normal metabolic pathways once it is served its purpose, and which is without carcinogenic or any other harmful long range potential problems.

The following is a list of desirable criteria for bioadhesives, one or more of which has not been met by the prior materials.

1. Ease of application.
2. Control of polymerization.
3. Flexibility of the resulting bond.
4. Bond strength.
5. Transparency.
6. Low toxicity.
7. Biodegradability.

SUMMARY OF THE INVENTION

The practical implementation of the above described techniques has been plagued with many problems. Contrary to prior practice however, we have unexpectedly discovered that the use of photoactivatable crosslinking reagents combined with amino acid-containing polymers produces a highly molecularly crosslinked product upon photoactivation. Collagen crosslinked by this method may then be used as a bioadhesive for sutureless closures of the eye or any other wound in the body, or as a superhydrated material for contact lenses, moist bandage contact lens material, lens or corneal implant material, a wet occlusive bandage, patch graft, implant material to replace silicone in cosmetic plastic surgery, artificial joint lining material or as a drug delivery mechanism which releases medication.

In addition, it is appreciated that this method is equally applicable to binding amino acid-containing polymers to other polymers or inorganic materials. Potential clinical applications of this technique would include cementing prosthetic devices securely into place and incorporating collagen centers into contact lenses.

Although the method described in our invention may be used to crosslink any polymer that contains amino acid groups, a preferred use of the method is to crosslink biocompatible (meaning that said polymers are not highly immunogenic, do not provoke an inflammatory response, and do not promote excessive fibrotic growth) amino acid-containing polymers, more preferably amino acid-containing polymers which are of animal origin, more preferably still amino acid-containing polymers which occur naturally as extracellular polymers or proteins, and most preferably collagen, combinations of different types of collagen, and combinations of collagen with proteoglycans (glucosaminoglycans, GAGs). The following description therefore, is mainly directed to the crosslinking of collagen, combinations of different types of collagen, and combinations of collagen with proteoglycans, but the invention is not intended to be restricted to this use.

In one embodiment of the invention, crosslinked collagen is produced which is useful as a bioadhesive. Tissue adhesives have been used in the past, but they suffer from several problems including toxicity and poor biocompatibility. Our adhesive, on the other hand, is non-toxic and biocompatible since it is made of collagen, the main structural component of mammalian tissues. In addition the material satisfies all the desirable criteria for bioadhesives listed above, including ease of application, ability to control polymerization, flexibility of application, ability to control polymerization, flexibility of the resulting bond, high bond strength, transparency, low toxicity and biodegradability.

In this embodiment, processed purified collagen is mixed with photoactivatable heterobifunctional crosslinking reagents. The conventional site on the crosslinker binds to the amino acid groups on the collagen molecules, leaving the other photoactivatable site unbound. This mixture is then applied to the tissue. With appropriate photoactivation, the photoactivated sites on the crosslinking reagents bind to the amino acid groups of collagen in the mixture and the collagen in the cornea, skin and other organs. A sutureless wound closure material is thus produced. As discussed above, controlling the polymerization rate of previously-known bioadhesives has been difficult. Rapid polymerization creates problems for the surgeon who must work quickly before the adhesive "sets." Our adhesive materials, however, can be applied to the cornea or other parts of the body and once the tissues are in the appropriate position, specific wavelengths of light may be used for final activation, thereby crosslinking, or setting the adhesive.

Other materials which are useful in accordance with all embodiments of the present invention are combinations of different types of collagen and combinations of collagen with proteoglycans. Certain combinations of collagen exhibit advantageous properties for biological implantation in vivo, e.g., have greater structural rigidity, show resistance to degradation, are readily manipulable, have greater biotolerability, and have lower immunostimulatory properties. Certain combinations of collagen with proteoglycans exhibit the beneficial property that they promote fibroblast cell migration to the site of implantation, and thereby promote the healing process.

In another embodiment of the invention, an unexpected superhydrated form of collagen is produced which has application in many areas of medicine. Collagen and other hydrated substances tend to dry out very quickly due to evaporation. This desiccation changes the characteristics of the collagen material. In the method of our invention, however, the molecular crosslinks of collagen molecules are an ideal water entrapment matrix, making it possible to have and retain an extremely high water content.

Superhydrated collagen produced by the method of our invention would be an extremely important contact lens material. Soft contact lenses presently dehydrate while on the human eye. They become uncomfortable and change their fit because of this dehydration. Our material used as a soft contact lens would provide an extremely comfortable lens which would not dehydrate.

In addition we propose that as a superhydrated lens implant material with water bound within its interstices, the intraocular lens will not adsorb medication to the extent of the hydrogel intraocular lens currently in use. This property of low adsorption is an important advantage of our material.

Our highly crosslinked collagen is also of great use to plastic surgeons who at present use silicone for implant surgery and inject collagen, which is not highly crosslinked, underneath the skin to eliminate wrinkles. The poorly crosslinked collagen presently used in these techniques must be periodically reinjected because it is subject to breakdown. The highly crosslinked collagen of our invention resists breakdown and is useful as a semipermanent or permanent implant or injection material for plastic surgeons to use in reconstructive and cosmetic surgery.

The superhydrated collagen gel produced by the method of our invention can have incorporated within it a low melting agarose gel containing drug mixture. The collagen may then be placed upon the tissue, where the low melting agarose gel dissolves, thus releasing the bound drug into a specific target area of the body.

BRIEF DESCRIPTION OF THE DRAWINGS

FIGS. 2a–2b show histologic diagrams for crosslinked collagen and uncrosslinked collagen.

FIGS. 3a–3b show histologic diagrams for crosslinked collagen and uncrosslinked collagen.

FIG. 4 is a graph of percent original weight versus time for the dehydration of crosslinked collagen lenticles and noncrosslinked collagen lenticles.

FIG. 7 is a table showing antibody titers in mice serum after implantation of various materials for use in accordance with the present invention.

FIGS. 8a–8b show the structural formula and chemical data of representative commercially available chemical crosslinkers.

FIG. 9 is a table summarizing the chemical properties of collagen.

FIG. 15a shows a diagramatic representation of the "suturing" of tissue materials as represented by a "dissected disc." FIG. 15b shows a microscopic view of the suture formed in FIG. 15a.

DETAILED DESCRIPTION OF THE INVENTION

Figure 1B:
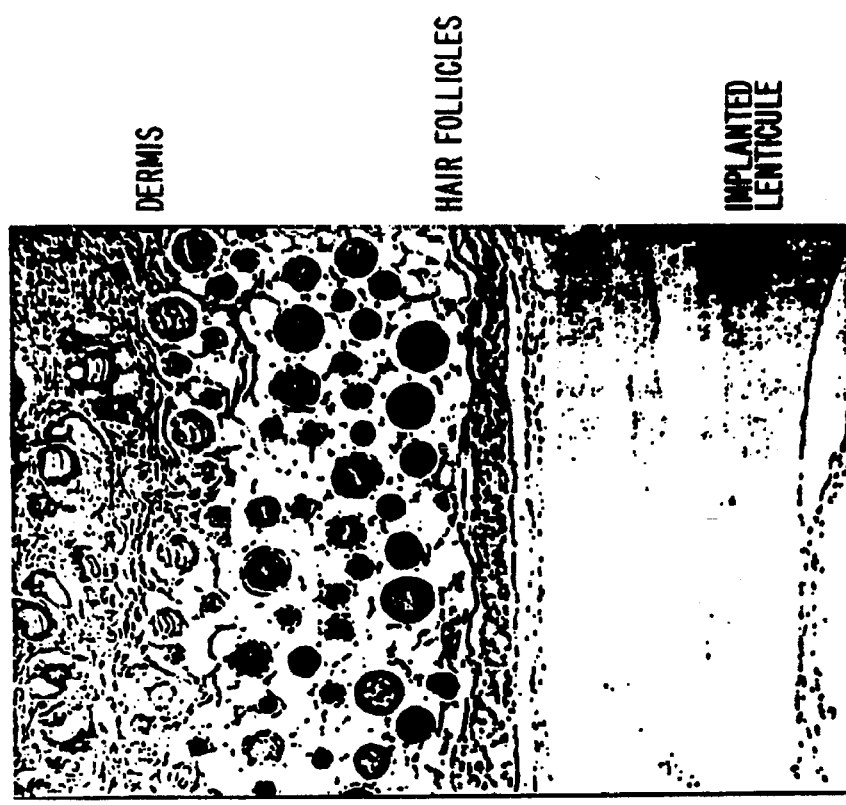
FIGS. 1a–1b show histologic diagrams for crosslinked collagen and uncrosslinked collagen.
Figure 1A:

To date, ten types of collagen have been identified based on their structural differences. Type I collagen is the most abundant in the cornea and has the lowest incidence of antigenicity.

Preferred embodiments of the crosslinking method of the invention use two commercial preparations of this Type I collagen—Vitrogen 100 (or other "Atelocollagen") and Rat Tail Type I. Vitrogen 100 is a purified pepsin-solubilized bovine dermal collagen made by Collagen Corp. In this collagen, the telopeptide responsible for the collagen molecule's antigenicity has been enzymatically cleaved. Rat Tail Type I is a non-pepsin treated collagen made by Collaborative Research, Inc.

Other preferred embodiments use combinations of different types of collagen or combinations of collagen and proteoglycans. For example, one embodiment makes use of a mixture of collagen type I and collagen type V, more preferably bovine collagen type I and human collagen type V, a human placental collagen type I and type V, or bovine collagen type I and human placental collagen type V, more preferably still collagen type I and collagen type V in a ratio of 1:1, 2:1, 3:1, 4:1, 5:1, 6:1, 7:1, 8:1, 9:1, or 10:1, most preferably a ratio of 3:1. Still other materials include combinations of human placental collagen types I, IV, V, and/or IX, kangaroo tail collagen type I, and/or rat tail collagen type I. An alternative embodiment makes use of cold fish skin gelatin, calf skin gelatin, and the like as materials having reduced immunostimulatory properties. A still further embodiment makes use of proteoglycans and/or combinations of collagen and proteoglycans which have the properties described in Stryer, Biochemistry, 3rd Edition, pp. 275–276. Proteoglycans exhibit the advantageous property of promoting influx of fibroblast cells to the area of implantation, and thereby promote the healing process.

The concentration of collagen in the method of the invention varies depending upon the intended use of the cross-linked product. The range may vary from 2.5 mg/ml to 10 mg/ml. These collagen preparation concentrations can be achieved by two well known methods: by dialyzing the collagen against acetate buffer at pH 5, or by lyophilizing known quantities of collagen and then resuspending the collagen in weak acids such as 0.012N HCL or $CH_3COOH$.

The pH of the collagen preparation can exist in a prowess range of pH 2.0 to the buffered preparation as established by Harry S. Geggel et al. ("Collagen Gel for Ocular Surface," Investigative Ophthalmology & Visual Sciences (1984), incorporated herein by reference) at a physiological pH of 7.4.

Crosslinking reagents are then added to the collagen preparation. Crosslinking techniques of our invention make use of heterobifunctional reagents which contain reactive groups that form a bridge between amino acid side chains on the collagen molecule. Bifunctional crosslinkers that may be used in the method of the invention include but are not limited to 4-azidobenzoic acid N-hydroxysuccinimide ester (HSAB) and 6-(4-azido-2-nitrophenyl-amino)hexanoic acid N-hydroxysuccinimide ester (SANAH). These crosslinkers are available from Sigma, Corp.

Unique to the method of the invention, is the fact that while one end of the bifunctional reagents form peptide-like bonds with the collagen amino acid side chains, the other end remains unbound until photoactivation by short-wave ultraviolet light. This end is then converted to a highly reactive compound called a "nitrene" or a "carbene," which in turn bonds with an amino acid side chain of either molecules of tissue collagen and/or collagen in the preparation.

The concentrations of the crosslinking reagent mixtures used in the invention may vary between 5 mM and 25 mM dissolved in a biologically compatible solvent such as DMSO. The concentration of the solvent cannot be less than 50% or the reagents will begin to precipitate. Optimum concentration of the crosslinking reagent is 10 mM established by collagen-reagent (photoactivated) mixture run on Tris-Borate Gels.

Photoactivation of the reagents can be achieved within a wavelength range of 220 nanometers (nm) to 310 nm. The optimum absorbing wavelength is approximately 265 nm with photoactivation time not to exceed 20 minutes. The duration of photoactivation, however, will vary depending on the type of crosslinker used.

The crosslinking efficiency of our reagent is highly dependent on the number of amino acid side chains it has available. In addition, excess crosslinker may hinder the crosslinking process due to potential competitive binding and internal rearrangement. This means that the active sites of the reagent bound to amino acid side chains via a peptide-like bonding process will be competed for by free reagent. To minimize this occurrence, the pre-photoactivated mixture of collagen and cross-linking reagent should be run through a Sephadex G-25 column. Fractions can be collected and run through a Spectrophotometer 260–320 nm for determination of peak collagen reagent fractions. The collected fractions can then be pooled and are ready for photoactivation.

The following examples are intended to illustrate further the practice of the invention and are not intended to limit the scope of the invention in any way.

EXAMPLE 1

Procedure for Buffered Collagen Preparation a. Using the method of R. Thoft ("Collagen Gel for Ocular Surface," Investig. Ophth. & Vis. Science) mix cold (4° C.) 0.2M $Na_2HPO_4$ in equal volume with 1.3M NaCl also at the same temperature. Add an equal volume of 0.1M NaOH to the buffer solution.

b. Add eight times (8×) volume of equivalent of Vitrogen to buffer solution.

c. Add cold Phenol red solution (5 mg/100 ml) if pH indicator is needed.

Note: The collagen concentration in the final preparation cannot be less than 1.45 mg/ml.

EXAMPLE 2

Procedure for Crosslinking Collagen a. Using the method of H. Geggel and R. Thoft (Investig. Ophth. & Visual Sciences, 1984), pooled fraction of a buffered collagen reagent mixture are poured into either 35 mm sterile culture dishes or polymethyl methacrylate (PMMA) bases lathed to specific curvatures and depth. Precrosslinked gel mixtures are kept at 4[degree]C. until ready for pretreatment and photoactivation.

b. The dishes or bases are then placed in a tissue culture water jacketed incubator at 37° C. with 5% $CO_2$, 95% air for 15 minutes.

c. The dishes or bases are then crosslinked by photoactivation with a short wave UV light (mineral light 254 mm UV lamp Model UVGL-25) for 15–20 minutes.

EXAMPLE 3

Procedure for Crosslinking Collagen a. Pooled fractions of buffered collagen reagent from Sephadex columns are poured into 35 mm sterile culture dishes or PMMA bases and kept at 4° C. until ready for use.

b. Using the method of T. Elsdale and T. Bard, J. (Cell Biol., 54:626–637, (1972), incorporated herein by reference), dishes or bases are placed in an ammonium hydroxide chamber for between 3 and 30 minutes depending on the degree of rigidity desired.

c. The gels are then photoactivated for 15–20 minutes to achieve crosslinking.

EXAMPLE 4

Washing and Storage of Crosslinked Gels a. Gels are removed from culture dishes and PMMA bases and washed twice with distilled $H_2O$.

b. Gels are placed on a glass plate and a 6 or 8 mm diameter trephine is used to punch out circular gels which are placed in individual test tubes containing 10 mL of phosphate buffer.

c. Fresh buffer is replaced every 60 minutes for 4 to 6 hours.

d. Gels are stored in Balanced Salt Solution or 0.9% sodium chloride.

Note: Continuous exhaustive washing may occur in PBS, BSS, NaCl (irrigation) or distilled $H_2O$.

EXAMPLE 5

Tissue Compatibility and Durability of Crosslinked Collagen Comprising Collagen Type I and Type V BALB/c mice (male, 6–8 weeks, 30 grams) were anaesthetized with Ketamine (50 mg/kg) and Xylazine (50 mg/kg) intraperitoneally.

Collagen lenticles were made by combining bovine collagen type I and human collagen type V (ratio 3:1) and HSAB crosslinker. The lenticles were dialyzed in sterile distilled water until all excessive HSAB was removed. They were soaked in gentamicin antibiotics for 4 hours. The non-crosslinked collagen lenticles were treated as described above.

The fur was shaven from the mid-scapular region of the mouse. The skin cleaned with iodine and a disposable size 10 scalpel to make a 2 cm incision through the skin into the subcutaneous region, sterile blunt scissors were used to tissue dissect through the subcutaneous tissue until a small pocket was formed. Lenticles of either HSAB crosslinked collagens or non-crosslinked collagen were placed into the subcutaneous pocket. The skin was closed with interrupted 6.0 prolene sutures. The sutures were removed at one week.

Animals were sacrificed with lethal intraperitoneal injections of Ketamine (150 mg/kg) and Xylazine (150 mg/kg) at 2 weeks, 1 month, 2 months and 3 months. The skin and subcutaneous tissues from the mid-scapular region were isolated and processed into paraffin blocks and sectioned for light microscopy. Sections were stained with either hematoxylin/eosin or Masson's Trichrome.

The mice tolerated the surgical procedure well without complications. The area of incision healed within a similar time period for the crosslinked and noncrosslinked lenticles. There was not any sign of abnormal inflammation or healing process. As seen histologically, at two weeks (see FIGS. 1a–3b) the non-crosslinked and crosslinked collagen lenticles were intact with connective tissue and fat surrounding the lenticles. At the edge of the were some polymorphonuclear cells and collagens (as seen with the Trichome stain). The lenticles appeared homogenous and devoid of cells.

After 3 months (see FIGS. 1a–3b), the sites of incisions had completely healed and fur had grown over the wound in both the crosslinked and non-crosslinked animals. Histologically, the lenticles were surrounded by fat cells, connective tissue cells and some areas of muscle. The non-crosslinked lenticle had cellular invasion at the periphery which seemed to leave small "holes or a Swiss-cheese appearance." In contrast, the crosslinked collagen did not have these areas of cellular invasion. The cells appeared to gather at the outer edge of the lenticle but did not infiltrate to the same degree as the non-crosslinked. The Masson's Trichrome stain showed that the lenticles stained a light blue while the heavy collagenous layers in the dermis stained dark blue. Again the non-crosslinked collagen had areas of cellular infiltration and what appeared to be digestion. The crosslinked collagens were more resistant and did not have the holes within the substance.

Prior to sacrifice, the serum was collected and antibody levels to type I collagen were measured. The crosslinked and non-crosslinked collagen lenticles had similar antibody levels to each other (see FIGS. 1a–3b).

These data indicate that, at 3 months, the HSAB crosslinked collagen lenticle appears more intact than the non-crosslinked collagen lenticle. Neither lenticle elicits an inflammatory response from the animal and they both healed at the same rate. Antibodies to type I collagen were at similar levels in the crosslinked and noncrosslinked animals.

EXAMPLE 6

Dehydration Rate of Crosslinked Collagen Lenticles Versus Noncrosslinked Collagen Lenticles Lenticles were made of either (a) Human placental collagen type I and type V (ratio 3:1) crosslinked with HSAB and UV light (b) Bovine type I collagen and human placental type V collagen (ratio 3:1) crosslinked with HSAB and UV light, (c) Bovine type I collagen and human placental type V collagen (ratio 3:1) crosslinked with 0.25% glutaraldehyde, (d) Bovine type I collagen crosslinked with 0.25 % glutaraldehyde. All lenticles were rinsed in a series of distilled water and then cut to identical size and thickness. Wet weights were measured at 0 hour and then hourly until the lenticles were completely dried as reflected by a constant weight. Data was calculated as % original weight.

The combination of bovine type I collagen and bovine type V collagen crosslinked with HSAB had the slowest dehydration rate, with 50% dehydration at a little over 2 hours. The lenticles made of bovine type I collagen crosslinked with glutaraldehyde dehydrated the quickest, with 50% dehydration at 55 minutes. (See FIG. 4.) The bovine lenticles were approximately 90% water. The combination of two collagen extended the dehydration time even without any crosslinker (data not shown). Dehydration rates were longer if chondroitin sulfate (2.3%) was added to the lenticle (data not shown). Rehydration of the lyophilized lenticle was 5–10 times faster (depending on the composition) in the crosslinked samples compared to the noncrosslinked ones.

These results indicate that the HSAB crosslinker made a more hydrophilic lenticle than glutaraldehyde crosslinked collagen. Also the addition of a second collagen extended the dehydration time both with and without the addition of crosslinker. The crosslinked collagen lenticle traps water and slowly releases it.

EXAMPLE 7

Transmission Electron Microscopy of Lenticles of Bovine Type I Collagen and Human Type V Collagen Crosslinked with HSAB and UV Light Lenticles made of bovine type I collagen and human type V collagen (ratio 3:1) were crosslinked with HSAB and UV light. Samples were rinsed thoroughly with water until excessive crosslinker was removed. Lenticles were fixed in 4% glutaraldehyde/paraformaldehyde, post-fixed in osmium tetroxide and embedded in Epon-Araldite resin. Sections were cut with a glass knife, stained and viewed with a transmission electron microscope.

Figure 5A:
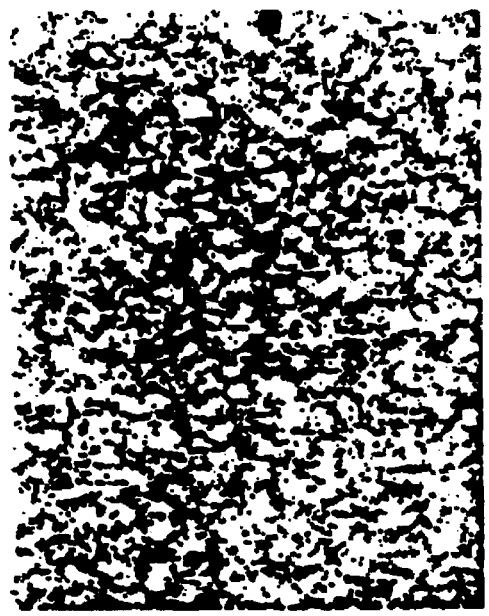
FIGS. 5a–5b show the transmission election micrographs of lenticles made of bovine type I collagen and human type V collagen crosslinked with HSAB and UV light.
Figure 5B:

The lenticles appeared as homogeneous fibrils randomly arranged with central pockets of "clear space" (see FIGS. 5a–5b). Higher magnification showed the fibrils to be similar in width and lacking any striations.

These results indicate that the HSAB crosslinked collagen lenticles retain their fibrillar nature with small randomly arranged fibrils and interfibrillar spaces.

EXAMPLE 8

Studies on the Properties of Cold Skin Fish Gelatins

Cold water fish skin gelatin in varying concentrations were used with and without HSAB or glutaraldehyde as the crosslinker. The fish skin gelatin had different properties compared to mammalian collagens. The fish skin gelatin is a brownish liquid and on SDS gel electrophoresis; it has multiple molecular weight bands. When we crosslinked the fish gelatin with either HSAB and UV light the result was a firm, hydrophilic, spongy-like gel that had a good consistency and could be manipulated with forceps or cut with a scalpel. In contrast, when it was fixed in glutaraldehyde, the lenticle became hard and almost plastic-like. When cut, the lenticle shattered into smaller fragments. This behavior was very different from the mammalian collagens.

The dehydration rate for the glutaraldehyde crosslinked fish gelatin was approximately 50% dehydration at 1¼ hours. This was increased to 3½ hours when chondroitin sulfate was added to the crosslinked fish gelatin.

On a gross levels of "stickiness between fingers," the uncrosslinked fish gelatin displayed stickiness while the mammalian collagens did not. With gel filtration we separated the fish gelatin fragments into those >300,000 kDa and those between 300,000–100,000 kDas. The repeated "stickiness between fingers" test showed that the >300,000 fraction retained its sticky behavior while the lower molecular weight material decreased in stickiness. When the >300,000 kDa fish gelatin was crosslinked with HSAB and made into a very thin sheet, then the sticky nature was retained. When a thin sheet of this material was placed onto the back of the hand, it stuck to the skin and did not come off until it was rubbed off.

Figure 6:
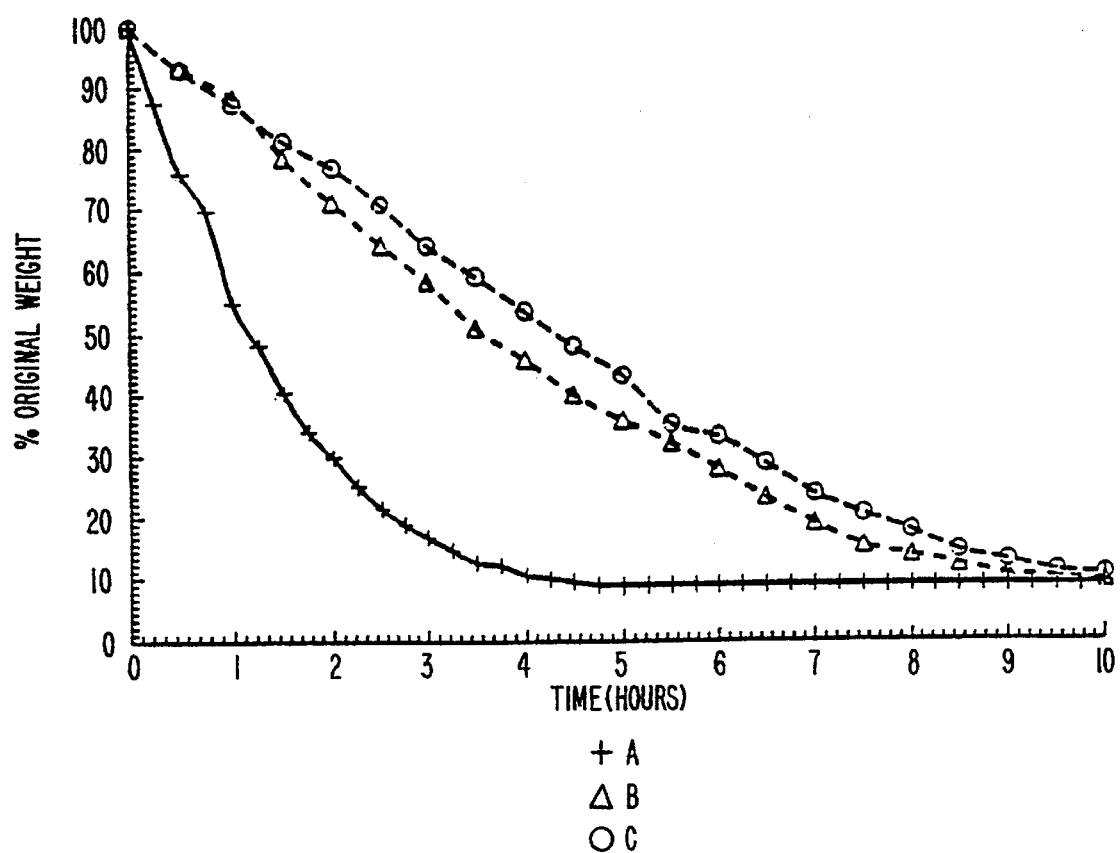
FIG. 6 is a graph of percent original weight versus time for the dehydration of crosslinked collagen lenticles and noncrosslinked collagen lenticles for gelatin.

Finally, a lenticle of HSAB crosslinked fish gelatin was placed into the mid-scapular region of mice. The animals were sacrificed at 2 weeks, 1 month, 2 months and 3 months, and the tissues prepared for light microscopy. Some sections were stained with hematoxylin/eosin and others with Mason's Trichrome. When viewed by light microscopy, the lenticle was dense and did not section well because it was too firm. There was minimal tissue reaction surrounding the lenticles and by 3 months there were a few cells which infiltrated the peripheral portion of the lenticles. At the time of sacrifice, serum was collected and the ELISA method was used to measure the antibodies to gelatins. There were no antibodies measured in any of the times examined (see FIG. 6).

These results indicate that cold fish skin gelatin behaves very differently from mammalian collagens or gelatin. Our studies suggest that it has a more sticky nature. It is tolerated within mice as well as the mammalian collagens.

EXAMPLE 9

Assessment of Immunostimulatory Effects of Various Collagen and Gelatin Compositions An ELISA assay with the mice serum was performed according to standard methodology well known in the art in order to assess the properties of various collagen and gelatin implant materials. The results are summarized in FIGS. 5a–5b.

EXAMPLE 10

Development of Biopolymeric Materials for Corneal Implant

Our experiments have focused on the creation of biopolymeric material which can be used as a transplant for correction of the acute and chronic pathologic conditions of the cornea.

Basic requirements for this material are:
chemical and biological inertness
transparency
high tensile strength
high hydrophility In order to create a product that would resemble that which it would replace, we sought ingredients from living sources. One of these ingredients is collagen, a large molecular amino acid polymer, an abundant structural component of corneal tissues. At a simplistic level, collagen synthesis involves the following reactions:

poly addition reaction (growth of the polymer by addition of monomers to the active center after three initiation step);

the propagation steps (creating stereochemical structure);

the termination steps (stipulating molecular weight and molecular weight distribution);

several modification steps (hydroxylation, glycosylation)

polycondensation (microfilaments and fibers formation).

The normal structure of the cornea requires the presence not only of type I collagen—basic building material—but also regulatory collagens (types II and V) and stabilizing collagens (types IV and IX), the presence and ratio of which diversify with transition from primary to secondary corneal stroma.

The list of important corneal non-cellular components also includes glycosaminoglycans (GAGs)—cornerstone of the ground substance (on 66%-keratin sulfate), glycoproteins, albumins, globulins, glucose, cristalloids, and water.

In our experiments, we have advantageously used either already-manufactured product—0.3% solution of the type I collagen (vitrogen, celtrix), in 0.012 n hydrochloric acid, or lyophilized acid soluble collagen (types I, IV, V, IX; SIGMA*), the source of which was:

human placenta (collagen types I, IV, V, IX)

kangaroo tail (type I)

rat tail (type I)

As a result of the neutralization, the acidic collagen solution became a gel that was susceptible to drying and was unstable in different enzymes because of a loose structure which is lacking in intra- and interfilamentous connections.

Accordingly, our study was directed to the development of a modified collagen with new, useful, and beneficial qualities. In order to achieve this goal, priority has been given to the artificial and natural crosslinkers which promote the propagation steps and polycondensation of microfilaments.

Candidates for the artificial crosslinkers include crosslinkers that are homo- and heterobifunctional, photoactive, and those that do not require heat for photolysis of nitro-groups. Our final choice was the HSAB photoreactive crosslinker (FIGS. 8a–8b) for each of the following reasons:

it is specific to the amino groups of collagen molecules it does not yield to other crosslinkers in strength of the chemical bonds it reacts under conditions favorable to the final experiment in comparison to SIAB or sulfo-SIAB, which ineffective at pH <7.0 or after heating it is colorless (in comparison to red SANPAH or bright yellow DFNBD)

despite irritating action inherent to other crosslinkers, HSAB is relatively nontoxic (in comparison to DFNDB, which is considered highly toxic).

Water soluble solfo-HSAB is the most preferred because it is soluble in DMSO, and because it displays the best physical characteristics of the final product.

The number of moles of crosslinker required for the crosslinking of the 1 mole of collagen was calculated on the sum of lysin residues in different chains of different types of the collagen molecules (FIG. 9).

The ratio of crosslinker dry weight to the collagen dry weight is about 1:10 (taking into account slight excess of crosslinker).

Calculation of the DMSO volume based itself on capability of this unique solvent to keep the crosslinker in a dissolved condition after the addition of the 0.012N HCl (collagen solvent). The "critical ratio" for the solvent is determined through titration, which showed that the volume of HCL (or any other solution) preferably must not exceed 40% (65 parts of HCl to 100 parts of DMSO). With the rise of the HCl volume, DMSO couldn't any more keep up the HSAB in solution and the latter dropped out as precipitates (clear, slightly pink crystals which can have the shape of crosses or prisms depending upon external factors).

Further reactions were developed under conditions optimal for the crosslinking reaction:

Interaction of acidic solution of collagen with solution of HSAB in DMSO (t°=0°+4° C., t=15 minutes)

Neutralization of HCL in ammonium hydroxide chamber (t≈15') and creation of thin jelly firm Photoactivation of crosslinker by short wave (254 nm) UV light 1200 joules for each side of collagen film Dialysis, which removes the excess of both crosslinker and DMSO (potentially harmful for the living tissues).

Although these reactions appear promising, they are compromised because the "critical ratio" leads to partial neutralization (too much DMSO with pH around 7.0!) of acidic collagen solution and formation of the gel that makes further manipulations impossible. In order to minimize gel formation, we discovered that a sacrifice of the "critical ratio" can be compensated for by removing precipitated crosslinker by ultracentrifugation. As discussed above, different types of collagen from different sources were being used.

Regarding the various compositions and correlations of different components, it should be pointed out that:

We have not observed the best expected result from successive mixing and exposure of collagen types I, IV, V and IX (that is: structural, regulatory and stabilizing units).

The optimal composition was collagen type I (lyophilized vitrogen) and collagen V (acid soluble, from human placenta) in ratio 3:1.

Type V collagen has been found to have an influence on structural organization of collagen type I filaments. Type V first appear sin the cornea during the swelling of the primary stroma and persist constancy in mature (secondary) stroma which is extremely rich in this type of collagen.

Immunofluorescence histochemical analyses show that type V molecules occupy the epitopes of type I collagen (indirect evidence of close interaction in the human cornea) (Lisenmayer et al., Ann. of the New York Academy of Sciences, 580:143–159 (1990) and Linsenmayer et al., J. Cell Biol. 96:124–132 (1983), incorporated herein by reference).

Immunoelectro microscopic analyses (direct evidence) confirm previous conclusion (Linsenmayer et al., Ann. of the New York Academy of Sciences, 580:143–159 (1990) and Birk, et al., J. Cell Biol. 106:999–1008 (1988), incorporated herein by reference).

The presence and mount (%) of type V determines the diameter (inverse proportion) and visible striation (direct proportion) of type I collage fibrils (Linsenmayer et al., Ann. of the New York Academy of Sciences, 580:143–159 (1990) and Adachi et al., Connect. Tissue Res. 14:257–2665 (1986), incorporated herein by reference). The most important role of type V collagen in the cornea is that it acts as a regulatory protein in fibril segment fusion by altering the fibrillar surface and therefore inhibits or promotes lateral association (like a zipper). (Birk et al., Ann. New York Acad. Sci. 580:143–159 (1990), incorporated herein by reference.) After noting this information, we describe below the sequence physico-chemical procedures and quantitative compositions of all reagents in final (optimal) experiment:

1. HSAB-1.2 mg DMSO-0.150 ml
2. ADD: Collagen Type I-9.0 mg 0.012 n HCL-0.450 ml mixing, homogenizing, t°=0°+4° C.
3. ADD: Collagen TYPE V-3.0 mg ⇒ final ratio of collagens Type I to Type V=3:1
4. Heating at +37° C. during 2 minutes
5. Ultracentrifugation at 0°+4° C. during 2 minutes
6. Neutralization of supernatant in $NH_4OH$ chamber (until complete clearing=15 minutes)
7. Exposure to UV light (short wave 254 nm, 1200 joules for each side of collagen film)
8. Dialysis; storage in distilled water at 0°+4° C.

As shown above, the best results require the warming of modified collagen. We postulate that warming helps to disclose inaccessible lysin residues and make them available for covalent interaction with the crosslinker. Care must be taken with all manipulations of modified collagen because heating over 42° C. or longer than 2' in an acidic environment, and the combination of both can denature the collagen and disactivate the crosslinker. Mixing and homogenizing must be very gentle, and the surrounding temperature must be approximately 0° C. during these procedures.

The difficulties we have encountered, and possible ways to explain and void or eliminate these are described below:

1. Precipitation formation:

This problem is encountered when the composition of our solvents diverges from the "critical ratio" (% of DMSO has to be at least 60). The easiest way to reduce precipitation, as noted above, is by ultracentrifugation. Our method of precipitation disintegration with ultrasonification (U.S.) was not very successful. U.S. seemed to be:

A powerful weapon against precipitation;

An additional mixing force which makes tight globes of rehydrated collagen more friable and discloses the active for future reaction sites;

Reasonably safe, because it does not disrupt collagen macromolecules at temperatures near 0° C.

Regardless of these beneficial features, we have ruled out ultrasonification because after crushing, precipitates give a "milky" appearance to collagen and we have been unable to significantly improve its optical characteristics.

2. The difficulty to reach homogenic mass during mixing can be explained by:

The nature of lyophilized collagen (solvent comes inside slowly and process of dissolution is very unequal);

The temperature of the procedure (low temperature increases viscosity of the collagen solution);

The polycondensation immediately after type V collagen addition (solution is getting very thick);

The manual handling and visual control

It is therefore desirable to operate with more liquid solutions (=0.1–0.3%) and concentrate these just before gel formation.

Figure 10:
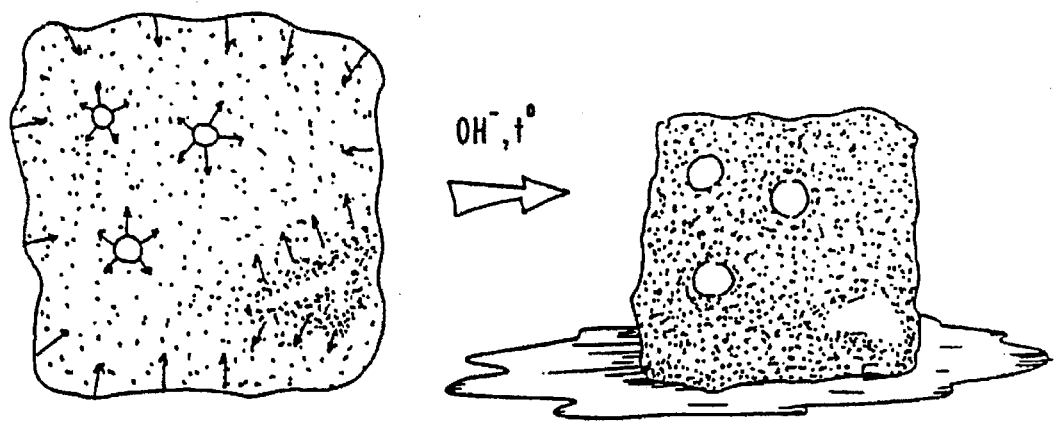
FIG. 10 shows a diagramatic explanation for the formation of small bubbles in a collagen solution or gel.

3. Formation of bubbles in the collagen solution or gel. There are three explanations:

(a) The bubbles are due to a gas dissolved in our materials and condensed on different "active sites" (crosslinker precipitation, dust particles, our particles) during warming;

(b) The bubbles arise because small bubbles that already persist in viscose solution grow with heating and get formation. When the gel sets, all the forces are pointing to the centers of the homogenous, chemically equal structures, and out of any surfaces and chemical or structural irregularities FIG. 10). These forces are squeezing out a small amount of water, increasing the size of the bubbles (there is a visible growth during neutralization) and increasing defects at the points of structural heterogeneities.

(c) The bubbles are possibly a by-product of a chemical reaction. It is also possible that combinations or all possibilities listed are involved. Centrifugation of modified collagen decreases the amount of bubbles dramatically. Probably, because it squeezes out small bubbles and removes some active sites that can promote gas condensation.

4. Yellowish color of modified collagen after exposure to UV light. This obligatory sign of crosslinking seems not a huge problem. The color is not so extensive to be able to destroy the color perception or be cosmetically unacceptable.

5. Haziness: An adequate treatment of this problem should begin with a discussion of the causes of the corneal transparency. Initially, the periodic structure of the corneal stroma includes:

equally sized fibrils all fibrils are strictly parallel to each other inside of single lamella rotation of parallel figures from one lamella to another is constant in space.

All these factors account for the cornea being not only transparent, but also incredibly strong, elastic and resistant to many external mechanical influences. We have discussed that optimal results are obtained when we are able to create similar periodic structure. The question therefore becomes how to make caustic collagen molecules (see the photo slides) to fall in one direction so that they could be "frozen" by crosslinker. The electrical charge of these molecules is equal almost to zero. Therefore, they cannot be straightened solely by an external electro-magnetic field. Although it is possible to charge collagen molecules by coupling them with "charge carriers," this technique would not accomplish molecule alignment because the external magnetic field would be pulling the collagen molecules at random sites in opposite directions. While there could be a possibility of strictly oriented resynthesis of new collagen molecule by using a charge carrier and external magnetic field of a synthetic matrix with fine filamentous unidirectional structure (procollagen I, carboxy- and aminopeptidases), such syntheses are very expensive. By using a synthetic matrix, we will probably be able to accomplish two goals (tensile strength and transparency) at once, and produce some variants of our product (crystal clear, but very fragile) acceptable for transplantation.

Alternatively, if we decide to use our optimally synthesized modified collagen which satisfies the requirements of transplantation, we have to decrease its haziness.

Figure 11:
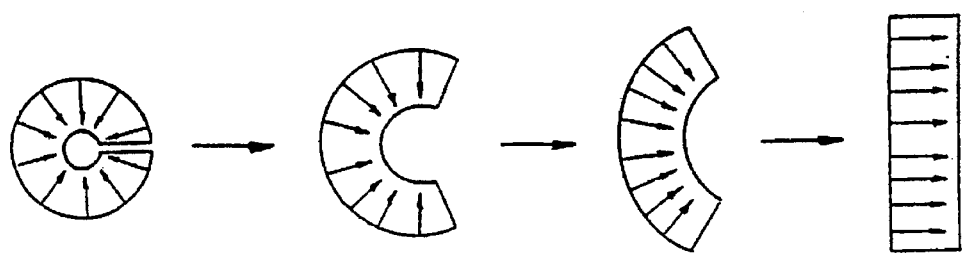
FIG. 11 shows the opening of a collagen disk such that one side is left available for contact with a neutralizing environment.
Figure 12:
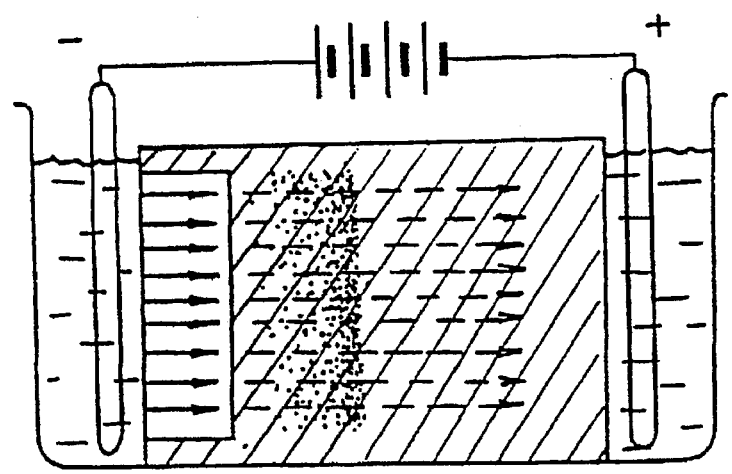
FIG. 12 shows a process for neutralization by using a potential difference (on modified collagen and+gel-acceptor).

We have discovered that with neutralization in $NM^uOH$ chamber, the modified collagen placed between two microslides gradually clears toward the center. The clarification process, however, is incomplete and consequently the final product (collagen disk) looks like a target with intensive cloudiness in the center (regardless of OH exposure time). Although the origin of this cloudiness is unclear, we understand that the process of ion exchange between the chamber (OH) and the collagen ($H^+$), negatively charged ions of different molecular weight are moving in the same direction as OH ions, which causes unequal haziness. In order to compensate for this effect, we open the collagen disk and leave only one side available for contact with the neutralizing environment. (FIG. 11) The other sides are blocked by a different gel, which plays the role of an acceptor for the negatively charged ions that create haziness in collagen disks. We can accelerate the process of neutralization by using a potential difference (on modified collagen and+on gel-acceptor). (FIG. 12)

Figure 13:
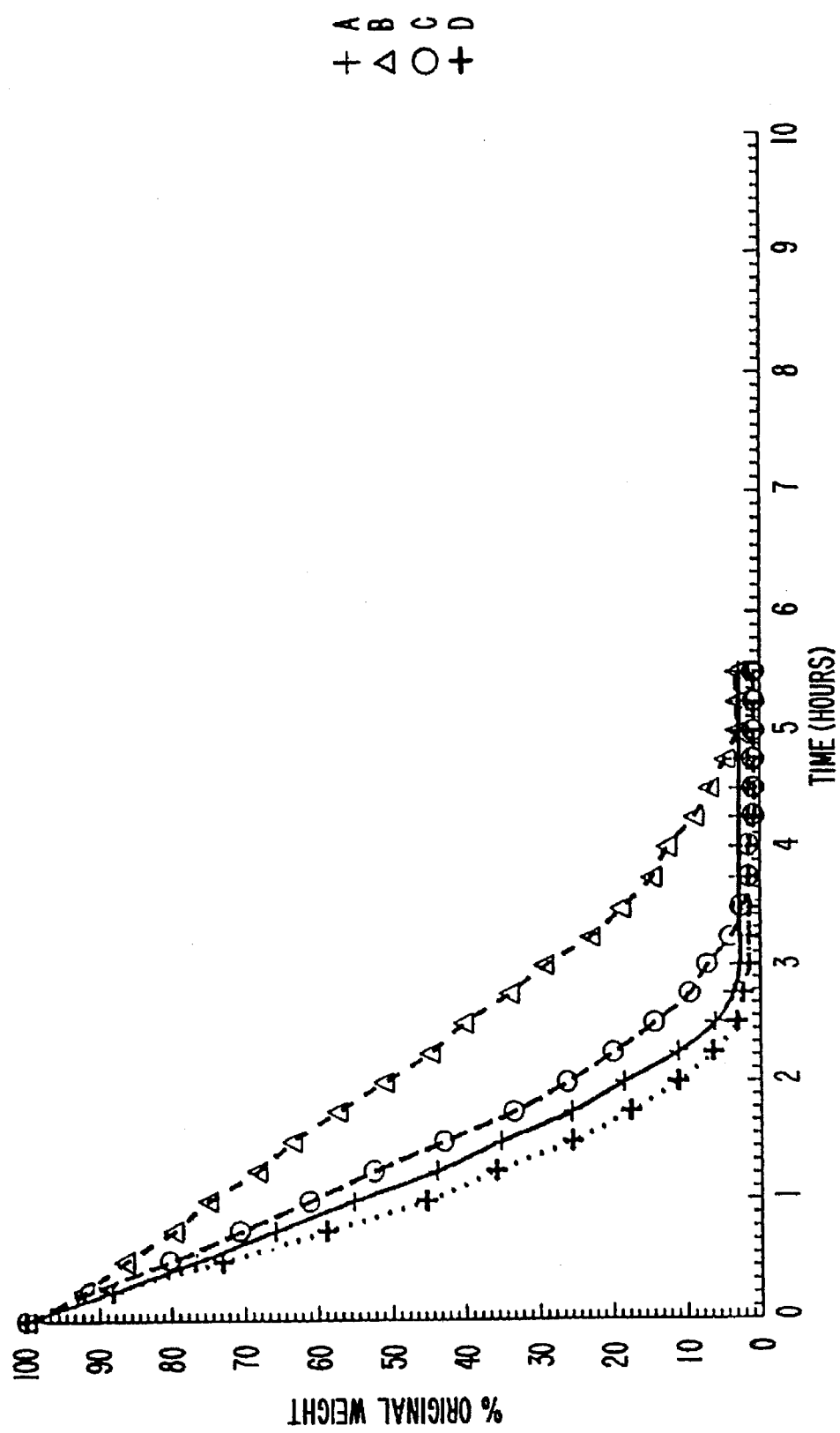
FIG. 13 is a graph of percent original weight versus time for the dehydration of crosslinked collagen lenticles and noncrosslinked collagen lenticles.

It should be noted that our final material was optimal not only in physico-chemical properties, but also in its ability to absorb and retain water. The half time of dehydration (FIG. 13) was approximately 70 minutes. At the same time, addition of type IV collagen to the optimal composition reduced T ½ up to several minutes. The presence of any second type of collagen extends dehydration time twice or more of its original IV without arbitral crosslinkers. It indicates that some types of collagen can work as natural crosslinkers. If the goal of dehydration is concentration of diluted solution, it has to be done without any additions (crosslinkers or collagens) to improve the subsequent results of different procedures.

Rehydration of lyophilized materials is 5–10 faster (demanding on composition) if they were pretreated with crosslinker. Our attempt to improve the characteristics of the final product with other homobifunctional amino specific crosslinkers, such as glutaraldehyde indicates that it does not make collagen clear, but increases its fragility and yellow color even in concentrations as low as 0.03%. Reaction with glutaraldehyde shows the presence of additional available amino groups, which have not reacted with HSAB (regardless of its excess).

In an effort to increase tensile strength, we have modified the collagen molecule. In collagen, the amount of free carboxyl groups exceeds the amount of amino groups ~1.42 times in the native collagen molecule. In order to increase the quantity of amino groups, we have tried to convert COOH to $-NH_2$ by reaction with ethylenediamine+carbodiimide (EDC). See Kurzer et al., Chem. Rev. 67, p. 107 (1967), incorporated herein by reference. The specific conditions of this multi-step reaction, however, have had pernicious effects on collagen molecules. We have discovered that EDS ($H_2N-CH_2-CH_2-NH_2$) ethylenediamine, can be used as an additional link between collagen molecules during reaction with an amino group specific crosslinker (like HSAB):

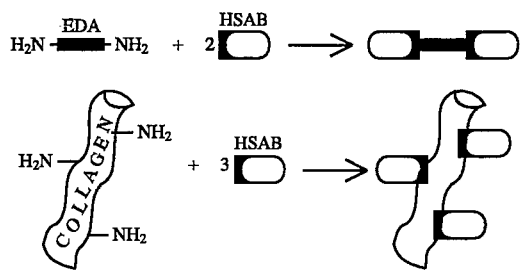

Using this embodiment, when all components are ready for the photoreactive step, UV light activated begins, and we observe the following reactions:

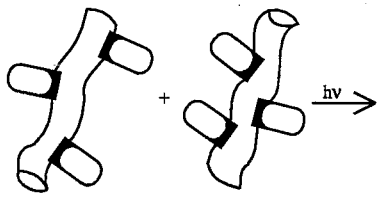

-continued

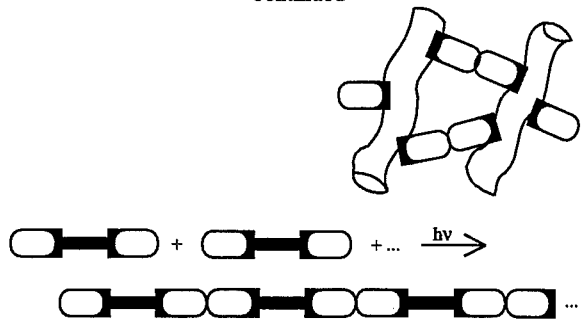

To obtain as a product:

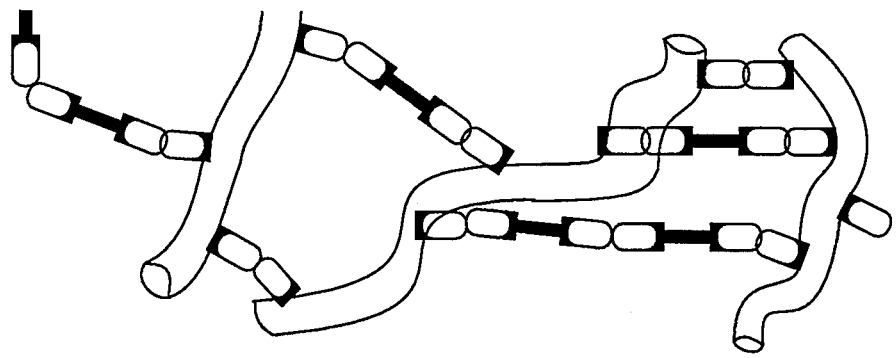

Different additions (chondroitin sulfate, dextran) improve the characteristics of the product. GAGs play an important role in the ground substance of the cornea and in the structural organization of collagen fibris. (For the first time GAGs were extracted by Woodin in 1952 (Woodin et al., Biochem. J. 51, p. 3198 (1952), incorporated herein by reference) and their composition was described 9 years later by Laurent and Anseth (Laurent et al., EXPTL Eye Res. 1,99.9 (1961), incorporated herein by reference). We have discovered that chondroitin sulfate extends into chemical interaction with collagen right after the contact between these two components. The product of this reaction was course fibers, similar to cellulose or cotton fibers. Tight and clear, they poorly retained water and were absolutely incomparable with the main goal of the experiments. An analogous reaction was described by Meyer in 1947 (Meyer, Physiol. Rev. 27, 45910 (1947), incorporated herein by reference). We have discovered that fibroblasts in healing would secret into the surrounding tissue space a mixture of hyaluronic acid, chemdroitia sulfate, and soluble collagen, and that under the influence of micropolysaccharides, soluble collagen precipitates as insoluble fibers (Meyer, Physiol. Rev. 27, 45910 (1947), incorporated herein by reference). GAGs are always present in the connective tissues, and are advantageous for use in preparations in accordance with the present invention because of their influence on the recipient's fibroblasts, and accordingly on the healing process.

EXAMPLE 11

Development of Implant Materials Including Gelatin from Cold Water Fish Skin

In this embodiment, we used not only different types of collagen, but also gelatin from cold water fish skin (48% liquid) and calf skin (powder). Interacting with water, gelatin forms lyophilic colloids-emulsions (like albumin or starch) and can be transformed into the semisolid gel (sol-gel reversible conversion with warming-cooling). Unlike homogeneous crystalloid solutions, all colloids are heterogeneous. They consist of two phases: particles (dispersed phase) and medium (dispersion Phase) (II). The important feature of gelatin is imbibition, that is, the taking up of fluid by a colloidal system resulting in swelling. The imbibition is affected by pH, temperature and concentration of electrolytes.

We have tested gelatin in different proportions with crosslinker. Glutaraldehyde proved to be the preferred crosslinker for effective interaction with gelatin. The optimal ratios of reagents are listed in Table 1.

TABLE 1

Concentration of gelatin and crosslinker in the gel film regarding to gelatin source

| SOURCE OF GELATIN | OPTIMAL CONCEN-TRATION | MINIMAL CONCEN-TRATION | GLUTARAL-DEHYDE CONCEN-TRATION |
| --- | --- | --- | --- |
| FISH SKIN | 10% | 6% | 0.25% |
| CALF SKIN | 7% | 3.25% | 0.25% |

Table 3 shows that the final products of crosslinking, having equal tensile strength, contain different quantifies of water: calf gelatin-93% and fish gelatin -90%.

Calf gelatin is more transparent and has a less intensive yellow coloration. Gelatin that had been pre-treated with ultrafiltration (M. W.>100,000 dalton) has much better qualities.

After filtration, it is more elastic, less tinted, has less swelling in the process of dialysis and is more stable in enzymes.

Figure 14:
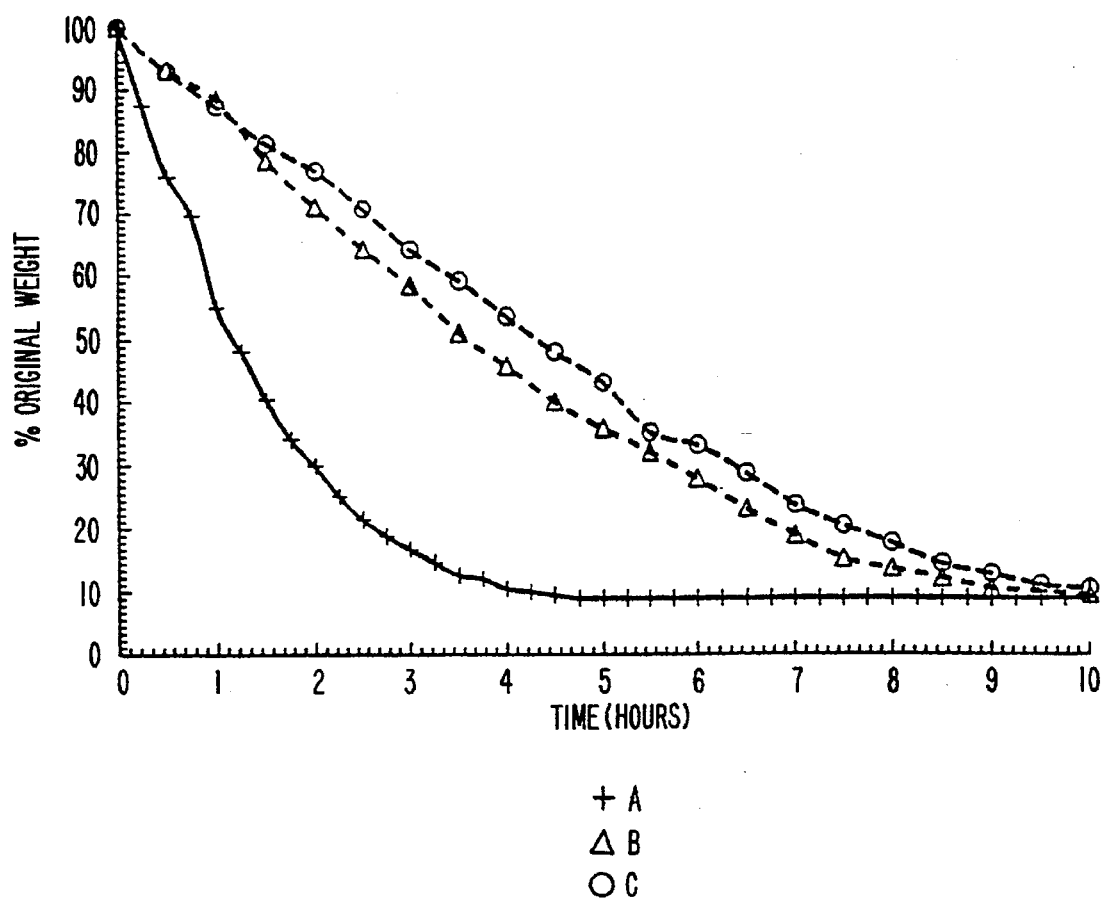
FIG. 14 is a graph of percent original weight versus time for the dehydration of crosslinked collagen lenticles and noncrosslinked collagen lenticles for gelatin.

Chondroitin sulfate makes gelatin more hydrophilic and extends the half-time of the dehydration as much as 3–4 times in a room environment. (FIG. 14).

Rehydration of the dried crosslinked gelatin that contains GAG should be carried out under a temperature near +20° C. By low temperature (near 0° C.), gelatin that contains GAG swells very much and the final volume of it turns out to be more than 10 times of its expected volume.

We have been able to successfully rehydrate uncrosslinked gelatin with glutaraldehyde-containing solution. Some of the factors which influence the ability to rehydrate uncrosslinked gelatin are listed below:

A. Oncotic pressure of the rehydrating solution
B. Concentration of the cross-linker
C. Temperature A. Macromolecules that were added by us to the rehydrating solution retain the water and thus increase the oncotic pressure. That prevents fast swelling of the dried gelatin films and makes process of the rehydration even and well-balanced. The best rehydrating solution is 4% chondroitin sulfate.

B. Crosslinker with concentration 1% (but not 0.25% as it was in preceding experiments) quickly ties molecules of gelatin in the superficial parts of dried film and prevents gelatin from immediate dissolving. (Solution with concentration 0.25% is ineffective.)

C. The temperature is directly proportionate to the time of rehydration.

Rehydrated gelatin films contain up to 98.5% of $H_2O$. They are fragile and slightly yellow, but very clear. They can be used for attachment to the cornea without sutures or intrastromally. They are also good as wet bandages for the burned surfaces and as a long-term drug delivery system. (In room environment, a film 1 mm thick retains the water about 10 hours!)

Dried uncrosslinked gelatin-GAG films (70% gelatin, 30% chondroitin sulfate) are extremely adhesive substances that are almost neutral optically. They stick tightly to any wet surface and probably could be used in superficial sutureless keratoplastics or epikeratophakis, with restricted water contact to prevent excessive swelling.

Making preparations for E.M. research, we have found one shortcoming of fish gelatin.

As prepared for the experiments, the lenticle was completely degraded in Osmium tetroxide solvent, the strong oxidizer.

Because we propose to transplant all tested products into living tissues which are rich in highly oxidative and digestive substances, it was decided to perform for them one more test—to check their resistance to some enzymes.

We discovered that fish gelatin, especially unfiltrated, containing both high molecular and low molecular types of fibers is very unstable to the action of peroxidase, Trypsin and collagenase B. If we take the time of digestion in the enzyme as the main index of stability, then we have determined that filtrated fish gelatin (all molecules are larger than 100,000 dalton) is 4 times more stable to the action of peroxidase than unfiltrated, it is 1–5 times more stable to the action of collagenase B and trypsin.

Addition of chondroitin sulfate increases by about ten times the stability of filtrated fish gelatin in trypsin, but does not intensify resistance to peroxidase and collagenase B. Calf gelatine, even unfiltrated, is 10 times more stable in collagenase B than treated fish gelatin. Being undigested, calf gelatin keeps itself in trypsin as much as 140 times longer!

For filtrated calf gelatin yet, but we hope that the results are even better.

In the process of testing collagen lenticles, we discovered an advantage of crosslinked collagen (Type I and Type V). It was resistant to digestion in collagenase B for 100 hours at room temperature, and remained stable in peroxidase and trypsin after a tenth day of experiment (150 times longer than uncrosslinked collagen).

EXAMPLE 12

Development of Chemical Sutures

We have also investigated the development of methods to make chemical sutures in order to join sharply disconnected tissues. As prototypes of living tissues were used:

untreated collagen gel crosslinked collagen gel crosslinked gelatin (filtrated, unfiltrated, from fish, from calf)

As materials for the chemical sutures were used:

NSAB

Sulfo-NSAB

Glutaraldehyde

Modified collage (with HSAB or Sulfo-HSAB; before neutralization)

Immediately prepared gelatin and glutaraldehyde (liquid during "sewing")

All "sutures" were tested in different combinations with tissues." Only one combination was successful where untreated collagen as "tissue" and modified collagen as "suture" were used.

After neutralization and exposure to UV-light, the "suture" did not differ from "tissues" by firmness. We have discussed that positive results for this experiment depends on the use of modified collagen (pH~5). This collagen returns acid-soluble and previously neutralized collagen again into solution. It provides molecules of "tissues" and "sutures" with ample opportunity for mutual diffusion.

For chemical sutures should be used a liquid carrier of the crosslinking agent, which changes aggregate state in the process of reaction.

We have changed the composition of sutures making them less dangerous for the recipient. Our results are described below, with reference to FIGS. 15a–15b.

Sutures: Crosslinker in a liquid phase, no carries.

Tissues: As was shown above.

The zone at contact is shown in FIG. 15b.

At magnification A, we see the irregularity of contact.

At magnification, B, we see a plurality of black dots.

These dots are "sutures"—molecules of crosslinker. Some of them have attached to lysin residues, some are disposed in inter-marginal space and some have migrated deeper between the collagen filaments, having been forced by chemical bonds. Every molecule of heterobifunctional photoreactive crosslinker must join with another crosslinker's molecule on the other side of the "wound." Only then are chemical sutures effective after UV-exposure. Homobifunctional crosslinker (glutaraldehyde) must join two amino groups, and again on the opposite sides of the "wound."

We tested also different combinations of collagen and glutaraldehyde types.

Type I collagen (vitrogen) reacts with 0.25% glutaraldehyde in the course of 15–20 minutes.

The final product is very clear and strong enough for the intralamellar implantation or simple superficial attachment, but considerable fragility of it makes impossible any manipulations with the sutures.

Combination of Types I and V collagen makes a final product considerably stronger and a little hazy.

In both cases, content of water in final products was 99%! In fact, it is pure water—a good material for contact lenses. But we have to note that the dehydration of that product is a practically irreversible process. All dehydrated samples were rather hydrophobic, and the rehydration was slow and very incomplete. We have discovered that this effect is caused by the length of crosslinker space ARM, and other homobifunctional amino group-specific crosslinker, which are longer in space, will promote rapid rehydration.

Different samples of "tissues" used in our studies on chemical "suturing," were placed into Petry dishes under unsterile conditions. Seven days later, the propagation of bacteria was revealed. In all cases, with one exception, the propagation of bacteria did not occur with crosslinked collagen. Crosslinked collagen therefore appears to be a bad medium for the propagation of bacteria, or the heterobifunctional photoreactive crosslinker exhibits bacteriostatic and/or bactericidic characteristics.

Modifications and variations of the present invention, and methods of use thereof, will be obvious to those skilled in the art from the foregoing detailed description. Such modifications and variations are intended to come within the scope of the appended claims.

What is claimed is:

1. A method of coupling amino acid-containing polymers, said method comprising the steps of:

providing a first collagen polymer and a second collagen polymer, with the proviso that the first collagen polymer and the second collagen polymer are of different collagens;

combining the first collagen polymer, the second collagen polymer, and a photoactivatable, heterobifunctional crosslinking agent having at least one photoactivatable site and at least one conventional site, wherein at least one said conventional site is coupled to at least one of said first collagen polymer and said second collagen polymer; and photoactivating the crosslinking agent, wherein at least one said photoactivatable site is coupled to the other of said first and said second collagen polymers in the combination.

2. The method of claim 1, wherein said first collagen polymer is collagen type I.

3. The method of claim 2, wherein said collagen type I is selected from the group consisting of bovine collagen type I and human placental collagen type I.

4. The method of claim 2, wherein said second collagen polymer is collagen type V, and wherein the ratio of the collagen type I to the collagen type V is 10:1 or less.

5. The method of claim 1, wherein said second collagen polymer is collagen type V.

6. The method of claim 5, wherein said collagen type V is human collagen type V.

7. The method of claim 1, wherein the photoactivatable, heterobifunctional crosslinking agent is selected from the group consisting of diazo compounds, aryl azide compounds, and alkyl azide compounds.

8. The method of claim 1, wherein said first collagen polymer is selected from the group consisting of human collagen types I, IV, V, and IX, and wherein said second collagen polymer is selected from the group consisting of nonhuman collagen types I, IV, V, and IX.

9. The method of claim 1, further comprising the step of combining said first and said second collagen polymers with a gelatin prior to photoactivating the crosslinking agent, said gelatin selected from the group consisting of fish skin gelatin and calf skin gelatin.

10. A coupled amino acid-containing polymer produced by the process defined in claim 1.

11. A coupled amino acid-containing polymer composition comprising:

a first collagen polymer;

a second collagen polymer; and a photoactivatable heterobifunctional crosslinking agent having at least one photoactivatable site and at least one conventional site, wherein at least one said photoactivatable site is coupled to at least one of said first collagen polymer and said second collagen polymer, and wherein at least one said conventional site is coupled to the other of said first and said second collagen polymers in the combination, with the proviso that the first collagen polymer and the second collagen polymer are of different collagens.

12. T The composition of Claim 11, wherein said first collagen polymer is collagen type I.

13. The composition of claim 12, wherein said second collagen polymer is collagen type V, and wherein the ratio of the collagen type I to the collagen type V is 10:1 or less.

14. The composition of claim 12, wherein said collagen type I is selected from the group consisting of bovine collagen type I and human placental collagen type I.

15. The composition of claim 11, wherein said second collagen polymer is collagen type V.

16. The composition of claim 15, wherein said collagen type V is human collagen type V.

17. The composition of claim 11, wherein the photoactivatable, heterobifunctional crosslinking agent is selected from the group consisting of diazo compounds, aryl azide compounds, and alkyl azide compounds.

18. The composition of claim 11, wherein said first collagen polymer is selected from the group consisting of human collagen types I, IV, V, and IX, and wherein said second collagen polymer is selected from the group consisting of nonhuman collagen types I, IV, V, and IX.

19. The composition of claim 11, further comprising the step of combining said first and said second collagen polymers with a gelatin prior to photoactivating the crosslinking agent, said gelatin selected from the group consisting of fish skin gelatin and calf skin gelatin.

20. A method of coupling amino acid-containing polymers, said method comprising the steps of:

combining an amino acid-containing polymer, a proteoglycan, and a photoactivatable, heterobifunctional crosslinking agent having at least one photoactivatable site and at least one conventional site, wherein at least one said conventional site is coupled to at least one of said amino acid-containing polymer and said proteoglycan; and photoactivating the crosslinking agent, wherein at least one said photoactivatable site is coupled to the other of said amino acid-containing polymer and said proteoglycan in the combination.

21. The method of claim 20, wherein said amino acid-containing polymer is collagen.

22. The method of claim 21, wherein said collagen is selected from the group consisting of collagen type I, IV, V, and IX.

23. A coupled amino acid-containing polymer produced by the process defined in claim 20.

24. A coupled amino acid-containing polymer composition comprising:

an amino acid-containing polymer;

a proteoglycan; and a photoactivatable heterobifunctional crosslinking agent having at least one photoactivatable site and at least one conventional site, wherein at least one said photoactivatable site is coupled to at least one of said amino acid-containing polymer and said proteoglycan, and wherein at least one said conventional site is coupled to the other of said amino acid-containing polymer and said proteoglycan in the combination.

25. The composition of claim 24, wherein said amino acid-containing polymer is collagen.

26. The composition of claim 25, wherein said collagen is selected from the group consisting of collagen type I, IV, V, and IX.

* * * * *